United States Patent [19]

Maravetz

[11] Patent Number: 4,705,557
[45] Date of Patent: Nov. 10, 1987

[54] HERBICIDAL 1-ARYL-Δ²-1,2,4-TRIAZOLIN-5-ONES AND SULFUR ANALOGS THEREOF

[75] Inventor: Lester L. Maravetz, Westfield, N.J.

[73] Assignee: FMC Corporation, Philadelphia, Pa.

[21] Appl. No.: 829,541

[22] Filed: Feb. 10, 1986

Related U.S. Application Data

[63] Continuation-in-part of Ser. No. 650,755, Sep. 13, 1984, abandoned, which is a continuation-in-part of Ser. No. 533,013, Sep. 15, 1983, abandoned.

[51] Int. Cl.$^4$ .................. A01N 43/36; C07D 249/12
[52] U.S. Cl. ........................ 71/92; 548/265; 548/263
[58] Field of Search .......... 548/265, 263, 264; 71/92

[56] References Cited

U.S. PATENT DOCUMENTS

| | | | |
|---|---|---|---|
| 3,922,162 | 11/1975 | Krenzer | 71/92 |
| 4,098,896 | 7/1978 | Edwards | 424/269 |
| 4,146,726 | 3/1979 | Konotsune et al. | 71/92 |
| 4,318,731 | 3/1982 | Kajioka et al. | 548/263 |
| 4,398,943 | 8/1983 | Kajioka et al. | 548/263 |
| 4,404,019 | 9/1983 | Uematsu et al. | 548/265 |
| 4,507,140 | 3/1985 | Sugavanam | 71/76 |

FOREIGN PATENT DOCUMENTS

| | | | |
|---|---|---|---|
| 56-32468 | of 1981 | Japan | 548/262 |
| 0053662 | 5/1981 | Japan | 548/265 |
| 78-3182 | 8/1978 | South Africa . | |

OTHER PUBLICATIONS

Nihon Nohyaku, "Herbicidal Delta 2-1,2,4-Triazolin-5-Ones", Chemical Abstracts: C.A., 95: 132895s(1981); abstract of Japanese Kokai 81-32,468 published 4/1/81.

*Primary Examiner*—Glennon H. Hollrah
*Assistant Examiner*—D. I. Dinner
*Attorney, Agent, or Firm*—Robert M. Kennedy; H. Robinson Ertelt

[57] ABSTRACT

Aryltriazolinones of the formula

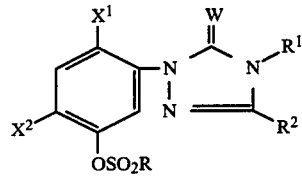

in which W is oxygen or sulfur, $X^1$ and $X^2$ are independently selected from halogen, haloalkyl, and alkyl, and R, $R^1$ and $R^2$ are selected from various radicals are disclosed as herbicides. Herbicidal efficacy and preparation of the compounds are described and exemplified.

27 Claims, No Drawings

HERBICIDAL 1-ARYL-Δ²-1,2,4-TRIAZOLIN-5-ONES AND SULFUR ANALOGS THEREOF

This application is a continuation-in-part of U.S. application Ser. No. 650,755, filed Sept. 13, 1984, now abandoned, which is a continuation-in-part of U.S. application Ser. No. 533,013, filed Sept. 15, 1983, now abandoned.

The invention described in this application pertains to weed control in agriculture, horticulture, or other fields where there is a desire to control unwanted plant growth. More specifically, the present application describes a series of novel herbicidal 1-aryl-Δ²-1,2,4-triazolin-5-ones and 5-thiones, herbicidal compositions of them, methods of preparing them, and methods for preventing or destroying undesired plant growth by preemergence or postemergence application of the herbicidal compositions to the locus where control is desired. The present compounds may be used to effectively control a variety of both grassy and broadleaf plant species. The present invention is particularly useful in agriculture, as a number of the novel herbicidal compounds described herein show a selectivity favorable to soybean, corn, cotton, wheat, rice, sunflower, or other crops at application levels which inhibit the growth of or destroy a variety of weeds.

Various herbicidal 1-aryl-Δ²-1,2,4-triazolin-5-ones are known in the art. U.S. Pat. No. 4,318,731 and corresponding British Pat. No. 2,056,971 disclose herbicidal aryltriazolinones of the formula

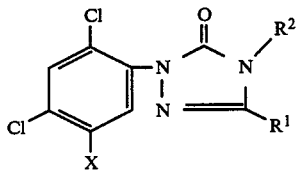

wherein $R^1$ is alkyl, $R^2$ is hydrogen, alkyl, or alkenyl, and X is hydroxy, alkyl, alkoxy, alkoxyalkoxy, alkenyloxy, or alkyloxycarbonylalkyloxy.

British Pat. No. 2,090,250, a continuation-in-part of the above British patent, adds to the above genus compounds wherein $R^2$ is alkynyl, halomethyl, or haloethyl, and X is alkoxy, alkenyloxy, alkynyloxy, alkoxyalkoxy, hydroxy, halomethyloxy, or haloethyloxy.

European Patent Application Publication No. 55,105 discloses a series of herbicidal aryltriazolinones of the formula

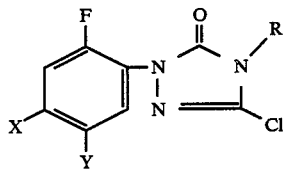

wherein R is alkyl, alkenyl, or cycloalkyl, X is chlorine or bromine, and Y is hydrogen or alkoxy.

Japanese Kokai No. 81-32,468 discloses herbicidal aryltriazolinones of the formula

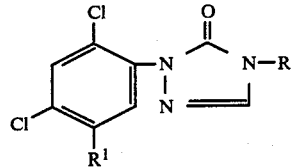

wherein R is hydrogen, alkyl, or 2-propenyl, and $R^1$ is methyl or alkoxy.

South African Patent Application No. 78/3182 discloses herbicidal aryltriazolinones, of the formula

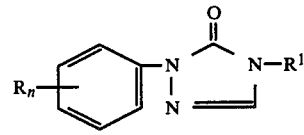

wherein $R_n$ is hydrogen or represents 1 to 4 same or different radicals selected from halogen, nitro, cyano, optionally halosubstituted alkyl, alkoxy, or alkylthio, and optionally substituted phenyl or phenoxy, and $R^1$ is alkyl, alkoxyalkyl, dialkoxyethyl, dialkylaminoethyl, or cycloalkyl.

U.S. Pat. No. 4,315,767 discloses herbicidal bicyclic compounds of the following formula

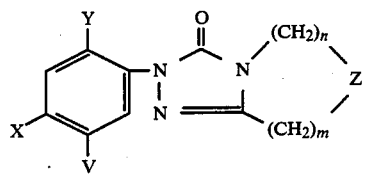

wherein V is hydrogen, halogen, methyl, or alkoxy, X is hydrogen, halogen, cyano, methyl, methoxy, or nitro, Y is hydrogen, halogen, or methyl, m and n are 0 to 4 (m plus n is 2 to 4), Q is oxygen or sulfur, and Z is oxygen, $S(O)_p$, or $NR^1$ wherein p is 0-2 and $R^1$ is alkyl, provided that when m plus n is 2 or 4 then Y and X are other than hydrogen, and when Z is $S(O)_p$ then n is 1 to 4.

Additional herbicidal bicyclic compounds based on aryltriazolinones are disclosed in U.S. Pat. No. 4,213,773 and have the following structural formula

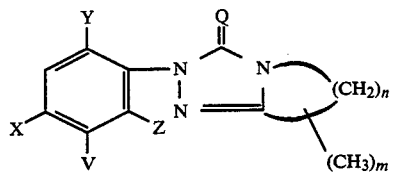

wherein V is hydrogen, halogen, hydroxy, alkyl, or —$OR^1$; $R^1$ is optionally substituted alkyl, cycloalkyl, cycloalkylalkyl, optionally substituted alkenyl, alkynyl, optionally substituted benzyl, alkylaminocarbonyl, (alkyl) (methyl or methoxy)aminocarbonyl, acyl, alkoxycarbonyl, or —$CHR^7R^8$ wherein $R^7$ is hydrogen or alkyl and $R^8$ is cyano, acetyl, hydroxycarbonyl, alkoxycarbonyl, hydroxymethyl, alkoxymethyl, alkylcarbonyloxymethyl, hydroxycarbonylethenyl, alkoxycarbonylethenyl, or a group —CO—$NR^{11}R^{12}$ wherein $R^{11}$ is hydrogen, alkyl, alkenyl, or alkoxy, and $R^{12}$ is hydrogen or alkyl; X is halogen, cyano, methyl, methoxy, or nitro; Y is hydrogen, halogen, or methyl; Z is hydrogen or halogen; n is 3–5; m is 0–2; and Q is oxygen or sulfur, with certain provisos.

A class of $\Delta^2$-1,2,4-triazolin-5-ones is disclosed as fungicides in U.S. Pat. No. 4,098,896. The disclosed genus has the formula

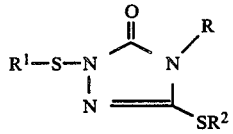

wherein R is alkyl, alkenyl, alkynyl, cycloalkyl, or optionally substituted phenyl or arylalkyl, $R^1$ is haloalkyl or haloalkenyl, and $R^2$ is optionally substituted alkyl, alkenyl, or alkynyl, or optionally substituted aryl, arylalkyl, or alkylaryl.

The present application describes a novel class of herbicidal 1-aryl-$\Delta^2$-1,2,4-triazolin-5-ones and 5-thiones characterized primarily in that the 1-aryl moiety is a 2,4,5-trisubstituted-phenyl group in which the C-5 substituent is a sulfonyloxy group $-OSO_2R$.

Any alkyl, alkenyl, or alkynyl group herein or the alkyl, alkenyl, or alkynyl portion of any group may be a straight chain or branched chain radical. Thus, 1-methylethyl, methylcyclopropyl, 2-methyl-2-propenyl, and 1-methyl-2-propynyl are branched chain examples of alkyl, cyclic alkyl, alkenyl, and alkynyl radicals respectively. Any halogen may be fluorine, chlorine, or bromine. Haloalkyl, haloalkenyl, and haloalkynyl radicals may have one or more same or different halogen atoms. Any aryl group or the aryl portion of any group may be a hydrocarbyl group such as phenyl or it may contain one or more heteroatoms such as in thienyl or furyl. Any aryl may be substituted, for example, with halogen or alkyl of 1 to 4 carbon atoms.

The compounds of this invention have the formula

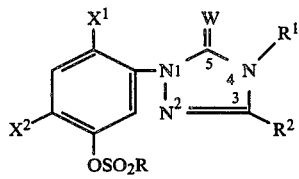

in which $X^1$ and $X^2$ are independently selected from halogen, haloalkyl, and alkyl;

W is oxygen or sulfur;

R is alkyl, haloalkyl, cyanoalkyl, arylalkyl, cyclic alkyl, alkenyl, haloalkenyl, arylalkenyl, alkynyl, haloalkynyl, arylalkynyl, aryl, or a group of the formula $-(CH_2)_mNR^3R^4$ or $-alkyl-Y-R^5$ wherein m is 0 to 5;

$R^1$ is alkyl, haloalkyl, cyanoalkyl, alkenyl, alkynyl, or a group of the formula $-alkyl-Y^1-R^6$;

$R^2$ is halogen, alkyl, cyanoalkyl, haloalkyl, arylalkyl, or a group of the formula $-alkyl-Y^2-R^7$;

$R^3$ is hydrogen or alkyl; $R^4$ is alkyl or a group of the formula $-alkyl-Y^3-R^8$;

$R^5$, $R^6$, $R^7$, and $R^8$ are independently alkyl, alkoxycarbonylalkyl, alkenyl, or alkynyl; and Y, $Y^1$, $Y^2$, and $Y^3$ are independently oxygen or $S(O)_r$ in which r is 0 to 2.

One aspect of the present invention pertains to the compounds of formula I above in which $X^1$ and $X^2$ are independently selected from halogen, haloalkyl of 1 to 3 carbon atoms, and alkyl of 1 to 5 carbon atoms;

W is oxygen or sulfur;

R is alkyl of 1 to 8 carbon atoms, haloalkyl, cyanoalkyl, or arylalkyl wherein each alkyl is of 1 to 5 carbon atoms, cyclic alkyl of 3 to 8 carbon atoms, alkenyl, haloalkenyl, or arylalkenyl wherein each alkenyl is of 2 to 5 carbon atoms, alkynyl, haloalkynyl, or arylalkynyl wherein each alkynyl is of 2 to 5 carbon atoms, aryl, or a group of the formula $-(CH_2)_mNR^3R^4$ or $(CH_2)_n-Y-R^5$ wherein m is 0 to 5 and n is 1 to 5;

$R^1$ is alkyl or haloalkyl of 1 to 5 carbon atoms, cyanoalkyl of 1 to 3 alkyl carbon atoms, alkenyl or alkynyl of 2 to 5 carbon atoms, or a group $(CH_2)_n-Y^1-R^6$ wherein n is 1 to 5;

$R^2$ is alkyl, haloalkyl, cyanoalkyl, or arylalkyl wherein each alkyl is of 1 to 3 carbon atoms, or a group $(CH_2)_n-Y^2-R^7$ wherein n is 1 to 5;

$R^3$ is hydrogen or alkyl of 1 to 5 carbon atoms;

$R^4$ is alkyl of 1 to 5 carbon atoms or a group $-CH_2-Y^3-R^8$;

$R^5$, $R^6$, $R^7$ and $R^8$, are independently alkyl of 1 to 5 carbon, atoms alkenyl or alkynyl of 2 to 5 carbon atoms, or a radical $-CH(R^9)CO_2R^{10}$;

$R^9$ is hydrogen or alkyl of 1 to 4 carbon atoms;

$R^{10}$ is alkyl of 1 to 4 carbon atoms; and

Y, $Y^1$, $Y^2$, and $Y^3$ are independently oxygen or $S(O)_r$ in which r is 0 or 2.

A number of interesting compounds within the above subgenus comprise the series wherein R is alkyl of 1 to 8 carbon atoms, haloalkyl, cyanoalkyl, or arylalkyl wherein each alkyl is of 1 to 5 carbon atoms, cyclic alkyl of 3 to 8 carbon atoms, alkenyl or haloalkenyl of 3 to 5 carbon atoms, alkynyl or haloalkynyl of 3 to 5 carbon atoms, or a group $(CH_2)_mNR^3R^4$ or $(CH_2)_n-Y-R^5$ wherein m is 0 to 3, n is 1 to 3, and $R^3$ and $R^4$ are independently alkyl of 1 to 5 carbon atoms.

Frequently, R will be alkyl of 1 to 5 carbon atoms, especially methyl; haloalkyl of 1 to 3 carbon atoms having one or more fluorine, chlorine, or bromine atoms; cyanoalkyl or phenylalkyl of 1 to 3 alkyl carbon atoms; cyclic alkyl of 3 to 6 carbon atoms; alkenyl or alkynyl of 3 to 5 carbon atoms; haloalkenyl of 3 to 5 carbon atoms such as a halopropenyl, for example, a halo-2-propenyl having one or more halogen atoms such as chlorine; haloalkynyl of 3 to 5 carbon atoms, especially a 3-halo-2-propynyl, a group of the formula $(CH_2)_mN(R^3)_2$ in which m is 0 or 2 and $R^3$ is alkyl of 1 to 5 carbon atoms such as methyl; or a group of the formula $(CH_2)_n-Y-R^5$ in which n is 1 or 2, especially 2, Y is oxygen or sulfur, and $R^5$ is alkyl of 1 to 5 carbon atoms such as methyl or ethyl, alkenyl or alkynyl of 3 to 5 carbon atoms, or a radical $-CH(R^9)CO_2R^{10}$ in which $R^9$ is hydrogen or methyl and $R^{10}$ is alkyl of 1 to 5 carbon atoms such as methyl or ethyl.

Examples of specific R substituents include methyl, ethyl, propyl, 1-methylethyl, butyl, 2-methylpropyl, 1-methylpropyl, 3-methylbutyl, chloromethyl, dichloromethyl, 3-chloropropyl, bromomethyl, difluoromethyl, trifluoromethyl, cyanomethyl benzyl, cyclopropyl, 2-propenyl, 2,3,3-trichloro-2-propenyl, 2-propynyl, 3-bromo-2-propynyl, dimethylamino, dimethylaminoethyl, 2-methoxyethyl, 2-ethoxyethyl, 2-(2-propenoxy)ethyl, 2-(2-propenthio)ethyl, 2-(2-propynoxy)ethyl, 2-(methoxycarbonylmethoxy)ethyl, and 2-(methoxycarbonylmethylthio)ethyl. R is preferably a methyl group.

W may be sulfur or, advantageously, oxygen.

The substituents $X^1$ and $X^2$ may be the same, and in such instances each will usually be a fluorine, chlorine, or bromine atom; less frequently, a methyl group. When $X^1$ and $X^2$ are different, $X^1$ will advantageously be fluorine or chlorine, preferably fluorine, and $X^2$ will frequently be selected from among chlorine, bromine, haloalkyl such as difluoromethyl, and alkyl such as methyl. $X^2$ is preferably chlorine.

The $R^1$ substituent is preferably a haloalkyl radical of 1 to 3 carbon atoms and having one or more independently selected halogen atoms, preferably selected from fluorine and chlorine; more preferably, a fluoroalkyl radical such as 3-fluoropropyl or, especially, difluoromethyl. Other $R^1$ substituents of particular interest include alkyl of 1 to 5 (preferably 1 to 3) carbon atoms, cyanoalkyl of 1 to 3 alkyl carbon atoms such as cyanomethyl, alkenyl of 3 to 5 carbon atoms especially 2-propenyl, alkynyl of 3 to 5 carbon atoms such as 2-propynyl, or a group $-(CH_2)_2-Y^1-R^6$ in which $Y^1$ is oxygen or sulfur and $R^6$ is alkyl of 1 to 5 (especially 1 or 2) carbon atoms such as methyl.

$R^2$ is preferably alkyl of 1 to 3 carbon atoms, especially methyl; haloalkyl of 1 to 3 carbon atoms, particularly a fluoroalkyl such as fluoromethyl or difluoromethyl; cyanoalkyl of 1 to 3 alkyl carbon atoms, for example, cyanomethyl; benzyl; or a group $-(CH_2)_n-Y^2-R^7$ in which n is 1 or 2, $Y^2$ is oxygen or sulfur, and $R^7$ is alkyl of 1 to 5 carbon atoms such as methyl or ethyl. $R^2$ will frequently and advantageously be fluoromethyl, difluoromethyl, or, especially, unsubstituted methyl.

Many of the present compounds may be prepared by sulfonylation of an appropriately substituted 5-hydroxyphenyltriazolinone (1a) or the thione analog (1b) with $RSO_2Cl$ or the equivalent in the presence of a base as illustrated in the following equation.

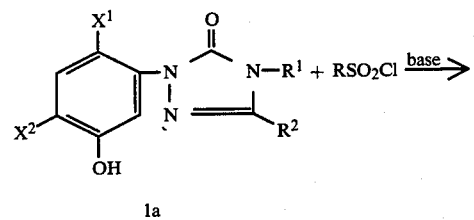

1a

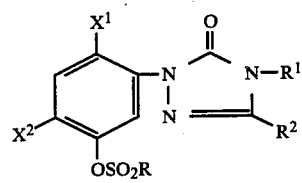

Ia

Sodium hydride and triethylamine are two bases that have been found to give satisfactory results, and their use in the preparation of representative compounds of the invention is described in detail in the examples below.

The aryltriazolin-5-thiones (W is sulfur) may be prepared by methods within the skill of the art, for example, by treating an appropriately substituted aryltriazolin-5-one with phosphorous pentasulfide in toluene under reflux conditions. The C=O to C=S conversion step may be conducted prior or subsequent to the addition of the $R^1$ substituent to the heterocyclic ring.

Compounds in which R is ethenyl may be prepared by reacting compound 1a or 1b with 2-chloroethanesulfonyl chloride in the presence of at least two equivalents of base. The second equivalent of base is used to effect dehydrochlorination on the chloroethyl radical to afford the ethenyl compound. Similarly, by the reverse type of reaction, the ethenyl compounds may be employed as substrates in addition reactions to prepare compounds in which R is $-(CH_2)_2-Y-R^5$ as illustrated in the equation below for a compound in which R is 2-(2-propenthio)ethyl.

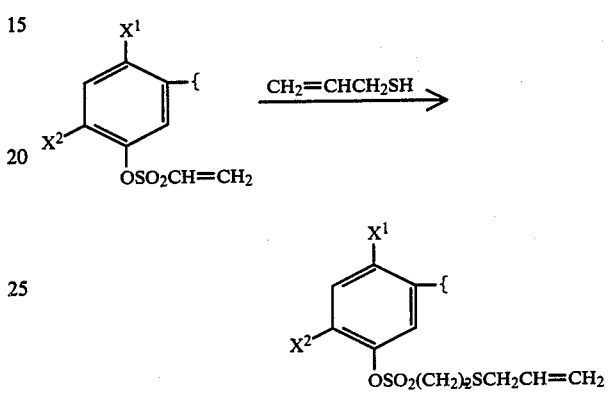

The sulfinyl or sulfonyl derivatives of the thio-adducts, i.e., Y is $S(O)_r$ wherein r is 1 or 2, are readily accessible by oxidation of the thio compounds.

The intermediate hydroxyphenyl compounds 1a are either known in the art and, therefore, are available by known methods, or may be prepared by methods analogous or similar to known methods or by methods within the skill of the art. For example, U.S. Pat. No. 4,318,731 and British Pat. No. 2,090,250, both of which are incorporated herein by reference, disclose preparation of a number of the present hydroxyphenyl intermediates 1a wheren $X^1$ and $X^2$ are chlorine atoms by dealkylation of the corresponding alkyloxyphenyl or alkenyloxyphenyl compound. This method was used herein to prepare many of the hydroxyphenyl intermediates 1a for the exemplary compounds by dealkylation of the corresponding isopropoxy or methoxy compound in the presence of concentrated sulfuric acid, a mixture of hydrobromic and acetic acids, or boron tribromide.

Further methods for preparing intermediate compounds are illustrated in the following chemical equations.

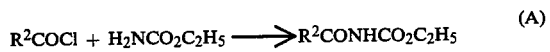

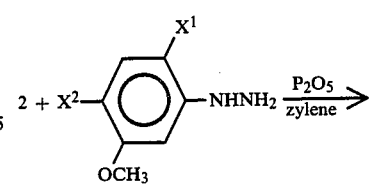

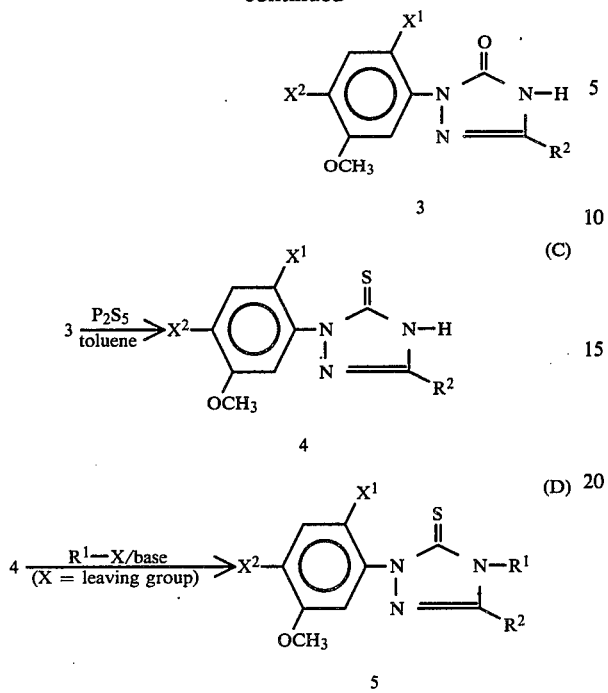
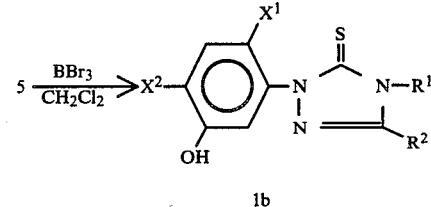
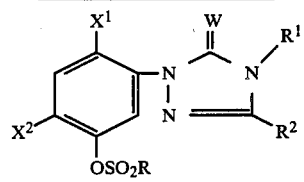

The preparation, properties, and herbicidal activity of representative herbicidal compounds of this invention are illustrated further in the examples below. All temperatures shown are in degrees Celsius, all pressures are in mm Hg, and reduced pressure for concentrations of liquid was produced by a water aspirator unless otherwise specified.

Representative compounds of the invention are identified by chemical structure in the following table wherein the compound numbers correspond to Example numbers.

TABLE 1

Representative Compounds

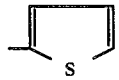

| Cpd. No. | $X^1$ | $X^2$ | R | $R^1$ | $R^2$ | W |
|---|---|---|---|---|---|---|
| 1 | Cl | Cl | $CH_3$ | $CF_2H$ | $CH_2$ | O |
| 2 | Cl | Cl | $CH_3$ | $CH_2CH=CH_2$ | $CH_3$ | O |
| 3 | Cl | Cl | $CH_2Cl$ | $CF_2H$ | $CH_3$ | O |
| 4 | Cl | Cl | $CH_2Cl$ | $CH_2CH=CH_2$ | $CH_3$ | O |
| 5 | Cl | Cl | $CF_3$ | $CF_2H$ | $CH_3$ | O |
| 6 | Cl | Cl | $CF_3$ | $CH_2CH=CH_2$ | $CH_3$ | O |
| 7 | Cl | Cl | $C_2H_5$ | $CF_2H$ | $CH_3$ | O |
| 8 | Cl | Cl | $C_2H_5$ | $CH_2CH=CH_2$ | $CH_3$ | O |
| 9 | Cl | Cl | $n\text{-}C_3H_7$ | $CF_2H$ | $CH_3$ | O |
| 10 | Cl | Cl | $n\text{-}C_3H_7$ | $CH_2CH=CH_2$ | $CH_2$ | O |
| 11 | Cl | Cl | $CH(CH_3)_2$ | $CF_2H$ | $CH_3$ | O |
| 12 | Cl | Cl | $CH(CH_3)_2$ | $CH_2CH=CH_2$ | $CH_3$ | O |
| 13 | Cl | Cl | $(CH_2)_2CH_2Cl$ | $CF_2H$ | $CH_3$ | O |
| 14 | Cl | Cl | $(CH_2)_2CH_2Cl$ | $CH_2CH=CH_2$ | $CH_3$ | O |
| 15 | Cl | Cl | $n\text{-}C_4H_9$ | $CF_2H$ | $CH_3$ | O |
| 16 | Cl | Cl | $n\text{-}C_4H_9$ | $CH_2CH=CH_2$ | $CH_3$ | O |
| 17 | Cl | Cl | $CH_2CH(CH_3)_2$ | $CF_2H$ | $CH_3$ | O |
| 18 | Cl | Cl | $CH(CH_3)C_2H_5$ | $CF_2H$ | $CH_3$ | O |
| 19 | Cl | Cl | $(CH_2)_2CH(CH_3)_2$ | $CF_2H$ | $CH_3$ | O |
| 20 | Cl | Cl | $CH=CH_2$ | $CF_2H$ | $CH_3$ | O |
| 21 | Cl | Cl | $NHCH_3$ | $CH_2CH=CH_2$ | $CH_3$ | O |
| 22 | Cl | Cl | $N(CH_3)_2$ | $CF_2H$ | $CH_3$ | O |
| 23 | Cl | Cl | $(CH_2)_2N(CH_3)_2$ | $CF_2H$ | $CH_3$ | O |
| 24 | Cl | Cl | $(CH_2)_2OCH_3$ | $CF_2H$ | $CH_3$ | O |
| 25 | Cl | Cl | $C_6H_5$ | $CF_2H$ | $CH_3$ | O |
| 26 | Cl | Cl | $C_6H_5$ | $CH_2CH=CH_2$ | $CH_3$ | O |
| 27 | Cl | Cl | $4\text{-}CH_3C_6H_4$ | $CF_2H$ | $CH_3$ | O |
| 28 | Cl | Cl | $4\text{-}CH_3C_6H_4$ | $CH_2CH=CH_2$ | $CH_3$ | O |
| 29 | Cl | Cl | $CH_2C_6H_5$ | $CF_2H$ | $CH_3$ | O |
| 30 | Cl | Cl | (thienyl) | $CF_2H$ | $CH_3$ | O |

TABLE 1-continued
Representative Compounds

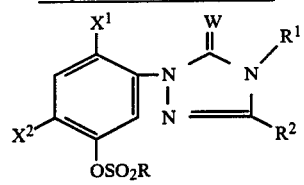

| Cpd. No. | $X^1$ | $X^2$ | R | $R^1$ | $R^2$ | W |
|---|---|---|---|---|---|---|
| 31 | Cl | Cl | CH=CHC$_6$H$_5$ | CF$_2$H | CH$_3$ | O |
| 32 | Cl | Cl | CH=CHC$_6$H$_5$ | CH$_2$CH=CH$_2$ | CH$_3$ | O |
| 33 | Cl | Cl | CH$_3$ | CH$_2$CH=CH$_2$ | Cl | O |
| 34 | Cl | Cl | CH(CH$_3$)$_2$ | CH$_2$CH=CH$_2$ | Cl | O |
| 35 | Cl | Cl | CH=CH$_2$ | CH$_2$CH=CH$_2$ | CH$_3$ | O |
| 36 | Cl | Cl | (CH$_2$)$_2$OC$_2$H$_5$ | CF$_2$H | CH$_3$ | O |
| 37 | Cl | Cl | (CH$_2$)$_2$OCH$_3$ | CH$_2$CH=CH$_2$ | CH$_3$ | O |
| 38 | Cl | Cl | CH$_3$ | n-C$_3$H$_7$ | CH$_3$ | O |
| 39 | Cl | Cl | CH$_3$ | CF$_2$CHClF | CH$_3$ | O |
| 40 | Br | Br | CH$_3$ | CF$_2$H | CH$_3$ | O |
| 41 | Br | Br | C$_2$H$_5$ | CF$_2$H | CH$_3$ | O |
| 42 | Br | Br | CH$_2$Cl | CF$_2$H | CH$_3$ | O |
| 43 | Br | Br | CF$_3$ | CF$_2$H | CH$_3$ | O |
| 44 | Cl | Cl | (CH$_2$)$_2$SCH$_2$CH=CH$_2$ | CF$_2$H | CH$_3$ | O |
| 45 | Cl | Cl | (CH$_2$)$_2$OCH$_2$CH=CH$_2$ | CF$_2$H | CH$_3$ | O |
| 46 | Cl | CH$_3$ | CH$_3$ | CF$_2$H | CH$_3$ | O |
| 47 | Cl | CH$_3$ | N(CH$_3$)$_2$ | CF$_2$H | CH$_3$ | O |
| 48 | Cl | CH$_3$ | C$_2$H$_5$ | CF$_2$H | CH$_3$ | O |
| 49 | Cl | CH$_3$ | CH$_2$Cl | CF$_2$H | CH$_3$ | O |
| 50 | Cl | Cl | (CH$_2$)$_2$OCH$_2$C≡CH | CF$_2$H | CH$_3$ | O |
| 51 | Cl | Cl | (CH$_2$)$_2$OCH$_2$CO$_2$CH$_3$ | CF$_2$H | CH$_3$ | O |
| 52 | F | Cl | CH$_3$ | CF$_2$H | CH$_3$ | O |
| 53 | Cl | Cl | CF$_2$H | CF$_2$H | CH$_3$ | O |
| 54 | Cl | Cl | CH$_3$ | CF$_2$H | C$_2$H$_5$ | O |
| 55 | F | Cl | CH$_3$ | CH$_2$CN | CH$_3$ | O |
| 56 | F | Cl | C$_2$H$_5$ | CF$_2$H | CH$_3$ | O |
| 57 | F | Cl | CH(CH$_3$)$_2$ | CF$_2$H | CH$_3$ | O |
| 58 | F | Cl | CH$_2$Cl | CF$_2$H | CH$_3$ | O |
| 59 | F | Cl | CHCl$_2$ | CF$_2$H | CH$_3$ | O |
| 60 | F | Cl | CF$_2$ | CF$_2$H | CH$_3$ | O |
| 61 | F | Cl | CH$_3$ | CH$_3$ | CH$_3$ | O |
| 62 | F | CH$_3$ | CH$_3$ | CF$_2$H | CH$_3$ | O |
| 63 | F | CH$_2$F | CH$_3$ | CF$_2$H | CH$_3$ | O |
| 64 | Cl | CH$_2$F | CH$_3$ | CF$_2$H | CH$_3$ | O |
| 65 | F | Cl | CH$_2$CN | CF$_2$H | CH$_3$ | O |
| 66 | F | Cl | CHCH$_2$CH$_2$ (cyclic) | CF$_2$H | CH$_3$ | O |
| 67 | F | Cl | CH$_2$C≡CH | CF$_2$H | CH$_3$ | O |
| 68 | F | Cl | CH$_2$CH=CH$_2$ | CF$_2$H | CH$_3$ | O |
| 69 | F | Cl | CH$_3$ | (CH$_2$)$_3$F | CH$_3$ | O |
| 70 | F | Cl | (CH$_2$)$_2$OCH$_3$ | CF$_2$H | CH$_3$ | O |
| 71 | F | Cl | (CH$_2$)OCH$_2$CO$_2$CH$_3$ | CF$_2$H | CH$_3$ | O |
| 72 | F | Cl | (CH$_2$)$_2$SCH$_2$CO$_2$CH$_3$ | CF$_2$H | CH$_3$ | O |
| 73 | F | Cl | CH$_3$ | CH$_2$C≡CH | CH$_3$ | O |
| 74 | F | Cl | CH$_3$ | (CH$_2$)$_2$SCH$_3$ | CH$_3$ | O |
| 75 | F | Cl | CH$_3$ | CF$_2$H | CF$_2$H | O |
| 76 | F | Cl | CH$_2$Br | CF$_2$H | CH$_3$ | O |
| 77 | F | Cl | CH$_3$ | CF$_2$H | CH$_2$CN | O |
| 78 | F | Cl | CH$_3$ | CF$_2$H | CH$_2$C$_6$H$_5$ | O |
| 79 | F | Cl | CH$_3$ | CF$_2$H | CH$_2$SCH$_3$ | O |
| 80 | Cl | F | CH$_3$ | CF$_2$H | CH$_3$ | O |
| 81 | F | Cl | CH$_3$ | CF$_2$H | CH$_2$OCH$_3$ | O |
| 82 | F | Cl | CH$_3$ | CF$_2$H | C$_2$H$_5$ | O |
| 83 | F | F | CH$_3$ | CF$_2$H | CH$_3$ | O |
| 84 | F | Cl | CH$_2$C(Cl)=CCl$_2$ | CF$_2$H | CH$_3$ | O |
| 85 | F | Cl | CH$_3$ | CFH$_2$ | CH$_3$ | O |
| 86 | F | Cl | CH$_3$ | CF$_2$H | CH$_3$ | S |
| 87 | F | Cl | CH$_2$Cl | CF$_2$H | CH$_3$ | S |
| 88 | Cl | Cl | CH$_3$ | CF$_2$H | CH$_3$ | S |
| 89 | F | Cl | CH$_3$ | CH$_2$CH=CH$_2$ | CH$_3$ | S |
| 90 | F | Cl | C$_2$H$_5$ | CH$_3$ | CH$_3$ | S |
| 91 | F | Br | CH$_3$ | CF$_2$H | CH$_3$ | O |
| 92 | Br | Cl | CH$_3$ | CF$_2$H | CH$_3$ | O |
| 93 | F | CF$_3$ | CH$_3$ | CF$_2$H | CH$_3$ | O |

Other representative compounds are those which are identical with compounds 1-90 respectively, except that $X^1$ is F and $X^2$ is Br. Still other representative compounds are those which are identical with compounds 1-90 respectively, except that $X^1$ is F and $X^2$ is $CF_3$. Other representative compounds are those which are identical with compounds 1-39 and 44-90 respectively except that $X^1$ is Br.

EXAMPLE 1

1-(2,4-Dichloro-5-Methylsulfonyloxyphenyl)-3-Methyl-4-Difluoromethyl-$\Delta^2$-1,2,4-Triazolin-5-One A stirred solution of 0.5 g (0.0016 mole) of 1-(2,4,-dichloro-5-hydroxyphenyl)-3-methyl-4-difluoromethyl-$\Delta^2$-1,2,4-triazolin-5-one and 0.2 g (0.002 mole) of triethylamine in 11 mL of tetrahydrofuran was cooled to 18° C., and 0.2 g (0.002 mole) of methanesulfonyl chloride was added dropwise. Upon complete addition, the reaction mixture was stirred at ambient temperature for 70 minutes, then 35-40 mL of water was added, and stirring was continued for an additional one hour. The resultant solid precipitate was collected by filtration, washed with water, then recrystallized from 1:1 ethanol-water to give 0.35 g of 1-(2,4-dichloro-5-methylsulfonyloxyphenyl)-3-methyl-4-difluoromethyl-$\Delta^2$-1,2,4-triazolin-5-one; m.p. 118°-120° C.

The nmr spectrum was consistent with the proposed structure.

Analysis calcd for $C_{11}H_9Cl_2F_2N_3O_4S$: C 34.04; H 2.34; N 10.82; Found: C 34.54; H 2.32; N 10.67.

EXAMPLE 2

1-(2,4-Dichloro-5-Methylsulfonyloxyphenyl)-3-Methyl-4-(2-Propenyl)-$\Delta^2$-1,2,4-Triazolin-5-One To a stirred solution of 0.75 g (0.0025 mole) of 1-(2,4-dichloro-5-hydroxyphenyl)-3-methyl-4-(2-propenyl)-$\Delta^2$-1,2,4-triazolin-5-one in 4 mL of dimethylformamide was added 0.06 g (0.0025 mole) of sodium hydride, then 0.29 g (0.0025 mole) of methanesulfonyl chloride. The reaction mixture was stirred at ambient temperature for 10 hours and the solvent removed under reduced pressure. The residue was dissolved in toluene then washed with water and aqueous 10% sodium hydroxide. The organic layer was dried with magnesium sulfate and filtered. The filtrate was concentrated under reduced pressure to give 0.89 g of desired product as an oil.

The nmr spectrum was consistent with the proposed structure.

EXAMPLE 3

1-(2,4-Dichloro-5-Chloromethylsulfonyloxyphenyl)-3-Methyl-4-Difluoromethyl-$\Delta^2$-1,2,4-Triazolin-5-One This compound was prepared by a method analogous to that of Example 1. The reaction of 0.5 g (0.0016 mole) of 1-(2,4-dichloro-5-hydroxyphenyl)-3-methyl-4-difluoromethyl-$\Delta^2$-1,2,4-triazolin-5-one with 0.25 g (0.0017 mole) of chloromethanesulfonyl chloride in the presence of 0.2 g (0.002 mole) of triethylamine and 11 mL of tetrahydrofuran gave 0.36 g of product, mp 80°-86° C.

The nmr spectrum was consistent with the proposed structure.

Analysis calcd for $C_{11}H_8Cl_3F_2N_3O_4S$: C 31.26; H 1.91; N 9.94; Found: C 31.26; H 2.55; N 9.75.

EXAMPLE 4

1-(2,4-Dichloro-5-Chloromethylsulfonyloxyphenyl)-3-Methyl-4-(2-Propenyl)-$\Delta^2$-1,2,4-Triazolin-5-One This compound was prepared by a method analogous to that of Example 1. The reaction of 1.0 g (0.003 mole) of 1-(2,4-dichloro-5-hydroxyphenyl)-3-methyl-4-(2-propenyl)-$\Delta^2$-1,2,4-triazolin-5-one with 0.50 g (0.003 mole) of chloromethanesulfonyl chloride in the presence of 0.34 g (0.003 mole) of triethylamine and 50 mL of tetrahydrofuran gave 0.8 g of the product as an oil.

The nmr spectrum was consistent with the proposed structure.

EXAMPLE 5

1-(2,4-Dichloro-5-Trifluoromethylsulfonyloxyphenyl)-3-Methyl-4-Difluoromethyl-$\Delta^2$-1,2,4-Triazolin-5-One To a stirred mixture of 0.7 g (0.002 mole) of 1-(2,4-dichloro-5-hydroxyphenyl)-3-methyl-4-difluoromethyl-$\Delta^2$-1,2,4-triazolin-5-one in 50 mL of chloroform was added 0.25 g (0.003 mole) of triethylamine. The mixture was cooled to 5° C., and 0.65 g (0.002 mole) of trifluoromethanesulfonic anhydride was added dropwise during a 3 minute period. Upon complete addition, the mixture was allowed to warm to ambient temperature with stirring over 3.3 hours. The reaction mixture was washed sequentially with water, aqueous 10% sodium hydroxide, aqueous 10% hydrochloric acid, aqueous saturated sodium bicarbonate solution, and water. The organic layer was dried over magnesium sulfate, filtered, and the filtrate concentrated under reduced pressure to give 0.8 g of 1-(2,4-dichloro-5-trifluoromethylsulfonyloxyphenyl)-3-methyl-4-difluoromethyl-$\Delta^2$-1,2,4-triazolin-5-one as an oil.

The nmr spectrum was consistent with the proposed structure.

Analysis calcd for $C_{11}H_{16}Cl_2F_5N_3O_4S$: C 29.88; H 1.37; N 9.50;

Found: C 31.87; H 1.81; N 8.66.

EXAMPLE 6

1-(2,4-Dichloro-5-Trifluoromethylsulfonyloxyphenyl)-3-Methyl-4-(2-Propenyl)-$\Delta^2$-1,2,4-Triazolin-5-one This compound was prepared by the reaction of 0.7 g (0.002 mole) of 1-(2,4-dichloro-5-hydroxyphenyl)-3-methyl-4-(2-propenyl)-$\Delta^2$-1,2,4-triazolin-5-one with 0.66 g (0.002 mole) of trifluoromethanesulfonic anhydride in the presence of 20 mL of pyridine. The product was obtained as an oil, 0.5 g.

The nmr spectrum was consistent with the proposed structure.

Analysis calcd for $C_{13}H_{10}Cl_2F_3N_3O_4S$: C 36.13; H 2.37; N 9.72;

Found: C 36.62; H 2.60; N 8.57.

EXAMPLE 7

1-(2,4-Dichloro-5-Ethylsulfonyloxyphenyl)-3-Methyl-4-Difluoromethyl-$\Delta^2$-1,2,4-Triazolin-5-One This compound was prepared by a method analogous to that of Example 1. The reaction of 0.5 g (0.0016 mole) of 1-(2,4-dichloro-5-hydroxyphenyl)-3-methyl-4-difluoromethyl-$\Delta^2$-1,2,4-triazolin-5-one with 0.22 g (0.0017 mole) of ethanesulfonyl chloride in the presence of 0.2 g (0.002 mole) of triethylamine and 11 mL of tetrahydrofuran gave 0.4 g of product, mp 83°-85° C.

The nmr spectrum was consistent with the proposed structure.

Analysis calcd for $C_{12}H_{11}Cl_2F_2N_3O_4S$: C 35.83; H 2.76; N 10.45;

Found: C 35.21; H 3.03; N 10.25.

EXAMPLE 8

1-(2,4-Dichloro-5-Ethylsulfonyloxyphenyl)-3-Methyl-4-(2-Propenyl)-$\Delta^2$-1,2,4-Triazolin-5-One This compound was prepared by a method analogous to that of Example 1. The reaction of 1.0 g (0.003 mole) of 1-(2,4-dichloro-5-hydroxyphenyl)-3-methyl-4-(2-propenyl)-$\Delta^2$-1,2,4-triazoline-5-one with 0.4 g (0.003 mole) of ethanesulfonyl chloride in the presence of 0.3 g (0.003 mole) of triethylamine and 50 mL of tetrahydrofuran gave 0.8 g of product as an oil.

The nmr spectrum was consistent with the proposed structure.

EXAMPLE 9

1-(2,4-Dichloro-5-Propylsulfonyloxyphenyl)-3-Methyl-4-Difluoromethyl-$\Delta^2$-1,2,4-Triazolin-5-One The compound was prepared by a method analogous to that of Example 1. The reaction of 1.0 g (0.0032 mole) of 1-(2,4-dichloro-5-hydroxyphenyl)-3-methyl-4-difluoromethyl-$\Delta^2$-1,2,4-triazolin-5-one with 0.51 g (0.0036 mole) of propanesulfonyl chloride in the presence of 0.38 g (0.004 mole) of triethylamine and 15 mL of tetrahydrofuran gave 1.05 g of product; mp 79°–82° C.

The nmr spectrum was consistent with the proposed structure.

Analysis calcd for $C_{13}H_{13}Cl_2F_2N_3O_4S$: C 37.51; H 3.15; N 10.10;

Found: C 37.44; H 2.96; N 10.01.

EXAMPLE 10

1-(2,4-Dichloro-5-Propylsulfonyloxyphenyl)-3-Methyl-4-(2-Propenyl)-$\Delta^2$-1,2,4-Triazolin-5-One This compound was prepared by a method analogous to that of Example 1. The reaction of 0.75 g (0.0025 mole) of 1-(2,4-dichloro-5-hydroxyphenyl)-3-methyl-4-(2-propenyl)-$\Delta^2$-1,2,4-triazolin-5-one with 0.36 g (0.0025 mole) of propanesulfonyl chloride in the presence of 0.25 g (0.0025 mole) of triethylamine in 50 mL of tetrahydrofuran gave 0.9 g of product as an oil.

The nmr spectrum was consistent with the proposed structure.

EXAMPLE 11

1-[2,4-Dichloro-5-(1-Methylethyl)sulfonyloxyphenyl]-3-Methyl-4-Difluoromethyl-$\Delta^2$-1,2,4-Triazolin-5-One The compound was prepared by a method analogous to that of Example 1. The reaction of 0.5 g (0.0016 mole) of 1-(2,4-dichloro-5-hydroxyphenyl)-3-methyl-4-difluoromethyl-$\Delta^2$-1,2,4-triazolin-5-one with 0.242 g (0.0017 mole) of 1-methylethanesulfonyl chloride in the presence of 0.2 g (0.002 mole) of triethylamine in 11 mL of tetrahydrofuran gave 0.23 g of product; mp 63°–66° C.

The nmr spectrum was consistent with the proposed structure.

Analysis calcd for $C_{13}H_{13}Cl_2F_2N_3O_4S$: C 37.51; H 3.15; N 10.10;

Found: C 38.24; H 3.81; N 9.39.

EXAMPLE 12

1-[2,4-Dichloro-5-(1-Methylethyl)Sulfonyloxyphenyl]-3-Methyl-4-(2-Propenyl)-$\Delta^2$-1,2,4-Triazolin-5-One This compound was prepared by a method analogous to that of Example 1. The reaction of 1.0 g (0.003 mole) of 1-(2,4-dichloro-5-hydroxyphenyl)-3-methyl-4-(2-propenyl)-$\Delta^2$-1,2,4-triazolin-5-one with 0.47 g (0.003 mole) of 1-methylethanesulfonyl chloride in the presence of 0.34 g (0.003 mole) of triethylamine in 50 mL of tetrahydrofuran gave 0.8 g of product as an oil.

The nmr spectrum was consistent with the proposed structure.

EXAMPLE 13

1-[2,4-Dichloro-5-(3-Chloropropyl)Sulfonyloxyphenyl]-3-Methyl-4-Difluoromethyl-$\Delta^2$-1,2,4-Triazolin-5-One The compound was prepared by a method analogous to that of Example 1. The reaction of 0.7 g (0.0023 mole) of 1-(2,4-dichloro-5-hydroxyphenyl)-3-methyl-4-difluoromethyl-$\Delta^2$-1,2,4-triazolin-5-one with 0.41 g (0.0023 mole) of 3-chloropropanesulfonyl chloride in the presence of 0.263 g (0.0026 mole) of triethylamine in 12 mL of tetrahydrofuran gave 0.42 g of product as an oil.

The nmr spectrum was consistent with the proposed structure.

Analysis calcd for $C_{13}H_{12}Cl_3F_2N_3O_4S$: C 34.65; H 2.68; N 9.32;

Found: C 36.50; H 3.13; N 8.67.

EXAMPLE 14

1-[2,4-Dichloro-5-(3-Chloropropyl)Sulfonyloxyphenyl]-3-Methyl-4-(2-Propenyl)-$\Delta^2$-1,2,4-Triazolin-5-One This compound was prepared by a method analogous to that of Example 1. The reaction of 1.0 g (0.003 mole) of 1-(2,4-dichloro-5-hydroxyphenyl)-3-methyl-4-(2-propenyl)-$\Delta^2$-1,2,4-triazolin-5-one with 0.59 g (0.003 mole) of 3-chloropropanesulfonyl chloride in the presence of 0.33 g (0.003 mole) of triethylamine in 10 mL of tetrahydrofuran gave 1.1 g of product as an oil.

The nmr spectrum was consistent with the proposed structure.

EXAMPLE 15

1-(2,4-Dichloro-5-Butylsulfonyloxyphenyl)-3-Methyl-4-Difluoromethyl-$\Delta^2$-1,2,4-Triazolin-5-One The compound was prepared by a method analogous to that of Example 1. The reaction of 0.62 g (0.002 mole) of 1-(2,4-dichloro-5-hydroxyphenyl)-3-methyl-4-difluoromethyl-$\Delta^2$-1,2,4-triazolin-5-one with 0.31 g (0.002 mole) of butanesulfonyl chloride in the presence of 0.22 g (0.002 mole) of triethylamine in 10 mL of tetrahydrofuran gave 0.73 g of product as an oil.

The nmr spectrum was consistent with the proposed structure.

Analysis calcd for $C_{14}H_{15}Cl_2F_2N_3O_4S$: C 39.08; H 3.51; N 9.77;

Found: C 40.24; H 3.77; N 9.27.

EXAMPLE 16

1-(2,4-Dichloro-5-Butylsulfonyloxyphenyl)-3-Methyl-4-(2-Propenyl)-$\Delta^2$-1,2,4-Triazolin-5-One This compound was prepared by a method analogous to that of Example 1. The reaction of 0.75 g (0.0025 mole) of 1-(2,4-dichloro-5-hydroxyphenyl)-3-methyl-4-(2-propenyl)-$\Delta^2$-1,2,4-triazolin-5-one with 0.39 g (0.0025 mole) of butanesulfonyl chloride in the presence of 0.25 g (0.0025 mole) of triethylamine in 50 mL of tetrahydrofuran gave 0.93 g of product as an oil.

The nmr spectrum was consistent with the proposed structure.

EXAMPLE 17

1-[2,4-Dichloro-5-(2-Methylpropyl)Sulfonyloxyphenyl]-3-Methyl-4-Difluoromethyl-$\Delta^2$-1,2,4-Triazolin-5-One The compound was prepared by a method analogous to that of Example 1. The reaction of 0.75 g (0.0024 mole) of 1-(2,4-dichloro-5-hydroxyphenyl)-3-methyl-4-difluoromethyl-$\Delta^2$-1,2,4-triazolin-5-one with 0.38 g (0.0024 mole) of 2-methylpropanesulfonyl chloride in the presence of 0.24 g (0.0024 mole) of triethylamine in 50 mL of tetrahydrofuran gave 0.38 g of product as an oil.

The nmr spectrum was consistent with the proposed structure.

EXAMPLE 18

1-[2,4-Dichloro-5-(1-Methylpropyl)Sulfonyloxyphenyl]-3-Methyl-4-Difluoromethyl-$\Delta^2$-1,2,4-Triazolin-5-One This compound was prepared by a method analogous to that of Example 1. The reaction of 0.9 g (0.003 mole) of 1-(2,4-dichloro-5-hydroxyphenyl)-3-methyl-4-difluoromethyl-$\Delta^2$-1,2,4-triazolin-5-one with 0.45 g (0.003 mole) of 1-methylpropanesulfonyl chloride in the presence of 0.29 g (0.003 mole) of triethylamine in 25 mL of tetrahydrofuran gave 0.44 g of product as an oil.

The nmr spectrum was consistent with the proposed structure.

Analysis calcd for $C_{14}H_{15}Cl_2F_2N_3O_4S$: C 39.08; H 3.51; N 9.77;
Found: C 40.42; H 3.71; N 8.80.

EXAMPLE 19

1-[2,4-Dichloro-5-(3-Methylbutyl)Sulfonyloxyphenyl]-3-Methyl-4-Difluoromethyl-$\Delta^2$-1,2,4-Triazolin-5-One The compound was prepared by a method analogous to that of Example 1. The reaction of 0.75 g (0.0024 mole) of 1-(2,4-dichloro-5-hydroxyphenyl)-3-methyl-4-difluoromethyl-$\Delta^2$-1,2,4-triazolin-5-one with 0.41 g (0.0024 mole) of 3-methylbutanesulfonyl chloride in the presence of 0.24 g (0.0024 mole) of triethylamine in 25 mL of tetrahydrofuran gave 0.27 g of product as an oil.

The nmr spectrum was consistent with the proposed structure.

Analysis calcd for $C_{15}H_{17}Cl_2F_2N_3O_4S$: C 40.55; H 3.86;
Found: C 41.13; H 3.97.

EXAMPLE 20

1-(2,4-Dichloro-5-Ethenylsulfonyloxyphenyl-3-Methyl-4-Difluoromethyl-$\Delta^2$-1,2,4-Triazolin-5-One The compound was prepared by a method analogous to that of Example 1. The reaction of 1.0 g (0.003 mole) of 1-(2,4-dichloro-5-hydroxyphenyl)-3-methyl-4-difluoromethyl-$\Delta^2$-1,2,4-triazolin-5-one with 0.56 g (0.003 mole) of 2-chloroethanesulfonyl chloride in the presence of 0.65 g (0.0064 mole) of triethylamine in 80 mL of tetrahydrofuran gave 0.25 g of product; mp 109°–112° C.

The nmr spectrum was consistent with the proposed structure.

Analysis calcd for $C_{12}H_9Cl_2F_2N_3O_4S$: C 36.02; H 2.27; N 10.50;
Found: C 36.40; H 2.33; N 10.41.

EXAMPLE 21

1-(2,4-Dichloro-5-Methylaminosulfonyloxyphenyl)-3-Methyl-4-(2-Propenyl)-$\Delta^2$-1,2,4-Triazolin-5-One By the method of Example 2, the reaction of 1-(2,4-dichloro-5-hydroxyphenyl)-3-methyl-4-(2-propenyl)-$\Delta^2$-1,2,4-triazolin-5-one and methylaminosulfonyl chloride in the presence of sodium hydride and dimethylformamide gave desired product as a waxy solid.

The nmr spectrum was consistent with the proposed structure.

EXAMPLE 22

1-(2,4-Dichloro-5-Dimethylaminosulfonyloxyphenyl)-3-Methyl-4-Difluoromethyl-$\Delta^2$-1,2,4-Triazolin-5-One This compound was prepared by a method analogous to that of Example 2. The reaction of 0.75 g (0.0024 mole) of 1-(2,4-dichloro-5-hydroxyphenyl)-3-methyl-4-difluoromethyl-$\Delta^2$-1,2,4-triazolin-5-one with 0.37 g (0.003 mole) of dimethylaminosulfonyl chloride in the presence of 0.072 g (0.003 mole) of sodium hydride in 9 mL of dimethylformamide gave 0.44 g of product; mp 114.5°–115.5° C.

The nmr spectrum was consistent with the proposed structure.

Analysis calcd for $C_{12}H_{12}Cl_2F_2N_4O_4S$: C 34.54; H 2.90; N 13.42;
Found: C 34.48; H 2.66; H 13.21.

EXAMPLE 23

1-[2,4-Dichloro-5-(2-Dimethylaminoethyl)Sulfonyloxyphenyl]-3-Methyl-4-Difluoromethyl-$\Delta^2$-1,2,4-Triazolin-5-One To a stirred solution of 0.5 g (0.0013 mole) of 1-(2,4-dichloro-5-ethenylsulfonyloxyphenyl)-3-methyl-4-difluoromethyl-$\Delta^2$-1,2,4-triazolin-5-one (Example 20) in 125 mL of diethyl ether was added gaseous dimethylamine via a gas dispersion tube below the surface of the solution. The addition was continued for 30 minutes after which the reaction mixture was flushed with dry nitrogen to remove excess amine. The reaction mixture was concentrated under reduced pressure to give a residual oil. The oil was redissolved in diethyl ether and washed with aqueous 10% sodium hydroxide and two portions of water. The organic layer was dried with magnesium sulfate and filtered. The filtrate was concentrated under reduced pressure to give 0.29 g of 1-[2,4-dichloro-5-(2-dimethylaminoethyl)sulfonyloxyphenyl]-3-methyl-4-difluoromethyl-$\Delta^2$-1,2,4-triazolin-5-one as an oil.

The nmr spectrum was consistent with the proposed structure.

EXAMPLE 24

1-[2,4-Dichloro-5-(2-Methoxyethyl)Sulfonyloxyphenyl]-3-Methyl-4-Difluoromethyl-$\Delta^2$-1,2,4-Triazolin-5-One To a stirred solution of 0.5 g (0.0013 mole) of 1-(2,4-dichloro-5-ethenylsulfonyloxyphenyl)-3-methyl-4-difluoromethyl-$\Delta^2$-1,2,4-triazolin-5-one (Example 20) in 25 mL of absolute methanol was added a catalytic amount of sodium methoxide. The reaction mixture was stirred at ambient temperature for 15 minutes, then warmed to 55° C. during two hours. The reaction mixture was concentrated under reduced pressure to give a residual oil. The oil was dissolved in diethyl ether and washed sequentially with aqueous 10% hydrochloric acid, water, aqueous 10% sodium hydroxide, and two portions of water. The organic layer was dried with magnesium sulfate and filtered. The filtrate was concentrated under reduced pressure to give 0.28 g of 1-[2,4-dichloro-5-(2-methoxyethyl)sulfonyloxyphenyl]-3-methyl-4-difluoromethyl-$\Delta^2$-1,2,4-triazolin-5-one as an oil.

The nmr spectrum was consistent with the proposed structure.

EXAMPLE 25

1-(2,4-Dichloro-5-Phenylsulfonyloxyphenyl)-3-Methyl-4-Difluoromethyl-$\Delta^2$-1,2,4-Triazolin-5-One By the method of Example 1, the reaction of 1-(2,4-dichloro-5-hydroxyphenyl)-3-methyl-4-difluoromethyl-$\Delta^2$-1,2,4-triazolin-5-one and benzenesulfonyl chloride in the presence of triethylamine and tetrahydrofuran gave the desired product, mp 126°–129° C.

The nmr spectrum was consistent with the proposed structure.

Analysis calcd for $C_{16}H_{11}Cl_2F_2N_3O_4S$: C 42.68; H 2.46; N 9.33;

Found: C 42.72; H 2.34; N 9.13.

EXAMPLE 26

1-(2,4-Dichloro-5-Phenylsulfonyloxyphenyl)-3-Methyl-4-(2-Propenyl)-$\Delta^2$-1,2,4-Triazolin-5-One By the method of Example 1, the reaction of 1-(2,4-dichloro-5-hydroxyphenyl)-3-methyl-4-(2-propenyl)-$\Delta^2$-1,2,4-triazolin-5-one and benzenesulfonyl chloride in the presence of triethylamine and tetrahydrofuran gave the desired product as an oil.

The nmr spectrum was consistent with the proposed structure.

EXAMPLE 27

1-[2,4-Dichloro-5-(4-Methylphenyl)Sulfonyloxyphenyl]-3-Methyl-4-Difluoromethyl-$\Delta^2$-1,2,4-Triazolin-5-One By the method of Example 1, the reaction of 1-(2,4-dichloro-5-hydroxyphenyl)-3-methyl-4-difluoromethyl-$\Delta^2$-1,2,4-triazolin-5-one adn p-toluenesulfonyl chloride in the presence of triethylamine and tetrahydrofuran gave the desired product, mp 160°–162° C.

The nmr spectrum was consistent with the proposed structure.

Analysis calcd for $C_{17}H_{13}Cl_2F_2N_3O_4S$: C 43.98; H 2.82; N 9.05;

Found: C 43.65; H 2.77; N 8.86.

EXAMPLE 28

1-[2,4-Dichloro-5-(4-Methylphenyl)Sulfonyloxyphenyl]-3-Methyl-4-(2-Propenyl)-$\Delta^2$-1,2,4-Triazolin-5-One By the method of Example 1, the reaction of 1-(2,4-dichloro-5-hydroxyphenyl-3-methyl-4-(2-propenyl)-$\Delta^2$-1,2,4-triazolin-5-one and p-toluenesulfonyl chloride in the presence of triethylamine and tetrahydrofuran gave the desired product as an oil.

The nmr spectrum was consistent with the proposed structure.

EXAMPLE 29

1-(2,4-Dichloro-5-Phenylmethylsulfonyloxyphenyl)-3-Methyl-4-Difluoromethyl-$\Delta^2$-1,2,4-Triazolin-5-One This compound was prepared by a method analogous to that of Example 1. The reaction of 0.94 g (0.003 mole) of 1-(2,4-dichloro-5-hydroxyphenyl)-3-methyl-4-difluoromethyl-$\Delta^2$-1,2,4-triazolin-5-one with 0.58 g (0.003 mole) of phenylmethanesulfonyl chloride in the presence of 0.31 g (0.003 mole) of triethylamine in 50 mL of tetrahydrofuran gave 0.75 g of product; mp 108°–111° C.

The nmr spectrum was consistent with the proposed structure.

EXAMPLE 30

1-[2,4-Dichloro-5-(2-Thienyl)Sulfonyloxyphenyl]-3-Methyl-4-Difluoromethyl-$\Delta^2$-1,2,4-Triazolin-5-One By the method of Example 1, the reaction of 1-(2,4-dichloro-5-hydroxyphenyl)-3-methyl-4-difluoromethyl-$\Delta^2$-1,2,4-triazolin-5-one and 2-thiophenesulfonyl chloride in the presence of triethylamine and tetrahydrofuran gave the desired product as a crystalline material, mp 133°–138° C.

The nmr spectrum was consistent with the proposed structure.

Analysis calcd for $C_{14}H_9Cl_2F_2N_3O_4S$: C 36.85; H 1.99; N 9.21;

Found: C 37.25; H 2.40; N 8.86.

EXAMPLE 31

1-[2,4-Dichloro-5-(2-Phenylethenyl)Sulfonyloxyphenyl]-3-Methyl-4-Difluoromethyl-$\Delta^2$-1,2,4-Triazolin-5-One By the method of Example 1, the reaction of b 1-(2,4-dichloro-5-hydroxyphenyl)-3-methyl-4-difluoromethyl-$\Delta^2$-1,2,4-triazolin-5-one and 2-(phenyl)ethenylsulfonyl chloride in the presence of triethylamine and tetrahydrofuran gave the desired product as a solid material.

The nmr spectrum was consistent with the proposed structure.

Analysis calcd for $C_{18}H_{18}Cl_2F_2N_3O_4S$: C 45.39; H 2.75; N 8.82;

Found: C 44.52; H 2.88; N 8.22.

EXAMPLE 32

1-[2,4-Dichloro-5-(2-Phenylethenyl)Sulfonyloxyphenyl]-3-Methyl-4-(2-Propenyl)-$\Delta^2$-1,2,4-Triazolin-5-One By method of Example 1, the reaction of 1-(2,4-dichloro-5-hydroxyphenyl)-3-methyl-4-(2-propenyl)-$\Delta^2$-1,2,4-triazolin-5-one and 2-(phenyl)ethenylsulfonyl chloride in the presence of triethylamine and tetrahydrofuran gave the desired product as an oil.

The nmr spectrum was consistent with the proposed structure.

EXAMPLE 33

1-[2,4-Dichloro-5-Methylsulfonyloxyphenyl]-3-Chloro-4-(2-Propenyl-$\Delta^2$-1,2,4-Triazolin-5-One This compound was prepared by a method analogous to that of Example 1. The reaction of 0.8 g (0.002 mole) of 1-(2,4-dichloro-5-hydroxyphenyl)-3-chloro-4-(2-propenyl)-$\Delta^2$-1,2,4-triazolin-5-one with 0.29 g (0.002 mole) of methanesulfonyl chloride in the presence of 0.25 g (0.002 mole) of triethylamine in 30 mL of tetrahydrofuran gave 0.99 g of product as a semi-solid The nmr spectrum was consistent with the proposed structure.

Analysis calcd for $C_{12}H_{10}Cl_3N_3O_4S$: C 34.59; H 2.90; N 10.08;
Found: C 35.12; H 2.55; N 9.37.

EXAMPLE 34

1-[2,4-Dichloro-5-(1-Methylethyl)Sulfonyloxyphenyl]-3-Chloro-4-(2-Propenyl)-$\Delta^2$-1,2,4-Triazolin-5-One This compound was prepared by a method analogous to that of Example 1. The reaction of 1.0 g (0.003 mole) of 1-(2,4-dichloro-5-hydroxyphenyl)-3-chloro-4-(2-propenyl)-$\Delta^2$-1,2,4-triazolin-5-one with 0.34 g (0.003 mole) of 1-methylethanesulfonyl chloride in the presence of 0.32 g (0.003 mole) of triethylamine in 30 mL of tetrahydrofuran gave 0.74 g of product; mp 106°–109° C.

The nmr spectrum was consistent with the proposed structure.

Analysis calcd for $C_{14}H_{14}C_2N_3O_4S$: C 37.81; H 3.63; N 9.45;
Found: C 37.60; H 3.00; N 9.21.

EXAMPLE 35

1-(2,4-Dichloro-5-Ethenylsulfonyloxyphenyl)-3-Methyl-4-(2-Propenyl)-$\Delta^2$-1,2,4-Triazolin-5-One By the method of Example 20 and Example 1, the reaction of 2.5 g (0.0083 mole) of 1-(2,4-dichloro-5-hydroxyphenyl)-3-methyl-4-(2-propenyl-$\Delta^2$-1,2,4-triazolin-5-one and 1.35 g (0.0083 mole) of 2-chloroethanesulfonyl chloride in the presence of 1.69 g (0.0167 mole) of triethylamine and 20 mL of tetrahydrofuran gave 1.9 g of product as an oil.

The nmr spectrum was consistent with the proposed structure.

EXAMPLE 36

1-[2,4-Dichloro-5-(2-Ethoxyethyl)Sulfonyloxyphenyl]-3-Methyl-4-Difluoromethyl-$\Delta^2$-1,2,4-Triazolin-5-One This compound was prepared by a method analogous to that of Example 24. The reaction of 0.7 g (0.002 mole) of 1-(2,4-dichloro-5-ethenylsulfonyloxyphenyl)-3-methyl-4-difluoromethyl-$\Delta^2$-1,2,4-triazolin-5-one (Example 20) and 20 mL of absolute ethanol in the presence of a catalytic amount of sodium metal gave 0.2 g of product; mp 152° C.

The nmr spectrum was consistent with the proposed structure.

EXAMPLE 37

1-[2,4-Dichloro-5-(2-Methoxyethyl)Sulfonyloxyphenyl]-3-Methyl-4-(2-Propenyl-$\Delta^2$-1,2,4-Triazolin-5-One This compound was prepared by a method analogous to that of Example 24. The reaction of 0.7 g (0.002 mole) of 1-(2,4-dichloro-5-ethenylsulfonyloxyphenyl)-3-methyl-4-(2-propenyl)-$\Delta^2$-1,2,4-triazolin-5-one (Example 35) and 100 mL of methanol in the presence of a catalytic amount of sodium methoxide gave 1.1 g of product as an oil.

The nmr spectrum was consistent with the proposed structure.

EXAMPLE 38

1-(2,4-Dichloro-5-Methylsulfonyloxyphenyl)-3-Methyl-4-Propyl-$\Delta^2$-1,2,4-Triazolin-5-One This compound was prepared by a method analogous to that of Example 1. The reaction of 0.78 g (0.003 mole) of 1-(2,4-dichloro-5-hydroxyphenyl)-3-methyl-4-propyl-$\Delta^2$-1,2,4-triazolin-5-one with 0.30 g (0.003 mole) of methanesulfonyl chloride in the presence of 0.29 g (0.003 mole) of triethylamine in 21 mL of tetrahydrofuran gave 0.94 g of product as an oil.

The nmr spectrum was consistent with the proposed structure.

EXAMPLE 39

1-(2,4-Dichloro-5-Methylsulfonyloxyphenyl)-3-Methyl-4-(2-Chloro-1,1,2-Trifluoroethyl)-$\Delta^2$-1,2,4-Triazolin-5-One This compound was prepared by a method analogous to that of Example 1. the reaction of 0.6 g (0.002 mole) of 1-(2,4-dichloro-5-hydroxyphenyl)-3-methyl-4-(2-chloro-1,1,2-trifluoroethyl)-$\Delta^2$-1,2,4-triazolin-5-one with 0.2 g (0.002 mole) of methanesulfonyl chloride in the presence of 0.18 g (0.002 mole) of triethylamine in 20 mL of tetrahydrofuran gave 0.42 g of product as an oil.

The nmr spectrum was consistent with the proposed structure.

EXAMPLE 40

1-(2,4-Dibromo-5-Methylsulfonyloxyphenyl)-3-Methyl-4-Difluoromethyl-$\Delta^2$-1,2,4-Triazolin-5-one Step 1: 3-Methoxyphenyl hydrazine A stirred solution of 50.0 g (0.41 mole) of 3-methoxyaniline in 60 mL of concentrated sulfuric acid and 100 mL of water was cooled to −5° C., and a solution of 28.0 g (0.41 mole) of sodium nitrite in water was added slowly while maintaining the temperature of the reaction mixture below 0° C. The mixture was stirred at 0° C. for 1 hour, then added slowly to a chilled, stirred solution of 100 g (0.44 mole) of stannous chloride dihydrate in 300 mL of concentrated hydrochloric acid. After complete addition, the reaction mixture was allowed to warm to ambient temperature and stand for 16 hours. The reaction mixture was filtered and the filter cake made basic. The basic material was extracted with diethyl ether. The reaction mixture filtrate was also made basic and extracted with diethyl ether. The ether extracts were combined and dried with magnesium sulfate. The mixture was filtered and the filtrate concentrated under reduced pressure to give 49.1 g of product as an oil.

The nmr spectrum was consistent with the proposed structure.

Step 2: Pyruvic acid, 3-methoxyphenyl hydrazone.

To a stirred solution of 45 g (0.33 mole) of 3-methoxyphenyl hydrazine in 400 mL aqueous 1N hydrochloric acid and 400 mL of ethanol was added dropwise a solution of 31.5 g (0.36 mole) of pyruvic acid in 30 mL of water. After complete addition, the reaction mixture was stirred at ambient temperature for 3 hours, and 200 mL of water was added. The mixture was filtered to give 56 g of product; mp 113°–114° C.

The nmr spectrum was consistent with the proposed structure.

Step 3: 1-(3-Methoxyphenyl)-3-methyl-$\Delta^2$-1,2,4-triazolin-5-one

To a stirred mixture of 55.5 g (0.27 mole) of pyruvic acid, 3-methoxyphenyl hydrazone in 1500 mL of toluene was added 27.0 g (0.27 mole) of triethylamine. The mixture was warmed until a clear solution formed. Diphenyl phosphoryl azide, 64.8 g (0.27 mole) was added at 35° C., and the reaction mixture was warmed to 75° C. and stirred until evolution of nitrogen stopped. The reaction mixture was heated to reflux temperature and stirred for 16 hours. The mixture was extracted with aqueous 10% sodium hydroxide. The extract was washed with toluene and made acidic. The resultant solid was collected by filtration and air dried to give 36.0 g of product; mp 143°–146° C.

The nmr spectrum was consistent with the proposed structure.

Step 4: 1-(3-Methoxyphenyl)-3-methyl-4-difluoromethyl-$\Delta^2$-1,2,4-triazolin-5-one To a stirred solution of 31.0 g (0.15 mole) of 1-(3-methoxyphenyl)-3-methyl-$\Delta^2$-1,2,4-triazolin-5-one, 31.0 g (0.10 mole) of tetrabutylammonium bromide, 31.0 g (0.77 mole) of sodium hydroxide in 1500 mL of cyclohexane was added 62.0 g (0.72 mole) of gaseous chlorodifluoromethane. The addition caused the reaction mixture to reflux. After complete addition, the reaction mixture was cooled. The supernatant liquid was decanted and washed sequentially with aqueous 10% hydrochloric acid, water, and aqueous 10% sodium hydroxide. The organic layer was dried with magnesium sulfate and filtered. The filtrate was concentrated under reduced pressure to give 28.0 g of product as a solid.

The nmr spectrum was consistent with the proposed structure.

Step 5: 1-(2,4-Dibromo-5-methoxyphenyl)-3-methyl-4-difluoromethyl-$\Delta^2$-1,2,4-triazolin-5-one To a stirred solution of 12.0 g (0.047 mole) of 1-(3-methoxyphenyl)-3-methyl-4-difluoromethyl-$\Delta^2$-1,2,4-triazolin-5-one in 75 mL of acetic acid was added dropwise 30.0 g (0.18 mole) of bromine. Upon complete addition, the reaction mixture was heated at reflux for 6 hours. The reaction mixture was concentrated under reduced pressure. The residue was dissolved in diethyl ether and washed with aqueous 10% sodium thiosulfate and water. The organic layer was dried with magnesium sulfate and filtered. The filtrate was concentrated under reduced pressure to give 17.4 g of product as a solid.

The nmr spectrum was consistent with the proposed structure.

Analysis calcd for $C_{11}H_9Br_2F_2N_3O_2$: C 32.00; H 2.20; N 10.17; Found: C 31.21; H 1.81; N 9.28.

Step 6: 1-(2,4-Dibromo-5-hydroxyphenyl)-3-methyl-4-difluoromethyl-$\Delta^2$-1,2,4-triazolin-5-one A solution of 17.2 g (0.042 mole) of 1-(2,4-dibromo-5-methoxyphenyl)-3-methyl-4-difluoromethyl-$\Delta^2$-1,2,4-triazolin-5-one in 100 mL of methylene chloride was added dropwise with stirring to 50.6 g (0.20 mole) of boron tribromide in methylene chloride. Upon complete addition, the reaction mixture was stirred at ambient temperature for 18 hours. The reaction mixture was washed with 50 mL of water. The organic layer was separated, dried with magnesium sulfate, and filtered. The filtrate was concentrated under reduced pressure to give 16.1 g of product; mp 137°–140° C.

The nmr spectrum was consistent with the proposed structure.

Step 7: 1-(2,4-Dibromo-5-methylsulfonyloxyphenyl)-3-methyl-4-difluoromethyl-$\Delta^2$-1,2,4-triazolin-5-one This compound was prepared by a method analogous to that of Example 2. The reaction of 1.0 g (0.003 mole) of 1-(2,4-dibromo-5-hydroxyphenyl)-3-methyl-4-difluoromethyl-$\Delta^2$-1,2,4-triazolin-5-one with 0.29 g (0.003 mole) of methanesulfonyl chloride in the presence of 0.6 g (0.003 mole) of sodium hydride in 50 mL of dimethylformamide gave 0.5 g of product; mp 129°–131° C.

The nmr spectrum was consistent with the proposed structure.

Analysis calcd for $C_{11}H_9Br_2F_2N_3O_2S$: C 27.69; H 1.90; N 8.81; Found: C 28.49; H 2.11; H 8.76.

EXAMPLE 41

1-(2,4-Dibromo-5-Ethylsulfonyloxyphenyl)-3-Methyl-4-Difluoromethyl-$\Delta^2$-1,2,4-Triazolin-5-One This compound was prepared by a method analogous to that of Example 2. The reaction of 1.0 g (0.003 mole) of 1-(2,4-dibromo-5-hydroxyphenyl)-3-methyl-4-difluoromethyl-$\Delta^2$-1,2,4-triazolin-5-one with 0.32 g (0.003 mole) of ethanesulfonyl chloride in the presence of 0.06 g (0.003 mole) of sodium hydride in 50 mL of dimethylformamide give 0.8 g of product as an oil.

The nmr spectrum was consistent with the proposed structure.

EXAMPLE 42

1-(2,4-Dibromo-5-Chloromethylsulfonyloxyphenyl)-3-Methyl-4-Difluoromethyl-$\Delta^2$-1,2,4-Triazolin-5-One This compound was prepared by a method analogous to that of Example 2. The reaction of 1.0 g (0.003 mole) of 1-(2,4-dibromo-5-hydroxyphenyl)-3-methyl-4-difluoromethyl-$\Delta^2$-1,2,4-triazolin-5-one with 0.37 g (0.003 mole) of chloromethanesulfonyl chloride in the presence of 0.06 g (0.003 mole) of sodium hydride in 50 ml of dimethylformamide gave 0.35 g of product as an oil.

The nmr spectrum was consistent with the proposed structure.

EXAMPLE 43

1-(2,4-Dibromo-5-Trifluoromethylsulfonyloxyphenyl-3-Methyl-4-Difluoromethyl-$\Delta^2$-1,2,4-Triazolin-5-One A stirred solution of 0.8 g (0.002 mole) of 1-(2,4-dibromo-5-hydroxyphenyl)-3-methyl-4-difluoromethyl-$\Delta^2$-1,2,4-triazolin-5-one and 0.2 g (0.002 mole) of triethylamine in 25 mL of chloroform was cooled to $-5°$ C. and 0.57 g (0.002 mole) of trifluoromethanesulfonic anhydride was added dropwise. Upon complete addition, the reaction mixture was allowed to warm to ambient temperature and was stirred for 60 hours. The reaction mixture was concentrated under reduced pressure to give a residue. The residue was dissolved in diethyl ether and washed with aqueous 10% sodium hydroxide. The organic layer was separated, dried with magnesium sulfate, filtered, and the filtrate concentrated under reduced pressure to give 0.4 g of product as an oil.

The nmr spectrum was consistent with the proposed structure.

EXAMPLE 44

1-{2,4-Dichloro-5-[2-(2-Propenethio)Ethylsulfonyloxy]Phenyl}-3-Methyl-4-Difluoromethyl-$\Delta^2$-1,2,4-Triazolin-5-One To a stirred solution of 0.5 g (0.0013 mole) of 1-(2,4-dichloro-5-ethenylsulfonyloxyphenyl)-3-methyl-4-difluoromethyl-$\Delta^2$-1,2,4-triazolin-5-one (Example 20) in 10 mL of tetrahydrofuran was added 0.09 g (0.0013 mole) of 2-propene-1-thiol, followed by a catalytic amount of powdered potassium hydroxide. Upon complete addition, the reaction mixture was stirred at ambient temperature for 18 hours. The reaction mixture was concentrated under reduced pressure to give a residue. The residue was slurried in water, then extracted with methylene chloride. The organic layer was washed with two portions of a saturated aqueous sodium chloride solution and dried with magnesium sulfate. The dried mixture was filtered and the filtrate concentrated under reduced pressure to give a residual oil. The oil was diluted with petroleum ether, then with hexane. The solvent was removed under reduced pressure to give 0.36 g of product as an oil.

The nmr spectrum was consistent with the proposed structure.

EXAMPLE 45

1-{2,4-Dichloro-5-[2-(2-Propenoxy)Ethylsulfonyloxy]-Phenyl}-3-Methyl-4-Difluoromethyl-$\Delta^2$-1,2,4-Triazolin-5-One This compound was prepared by a method analogous to that of Example 44. The reaction of 0.25 g (0.0006 mole) of 1-(2,4-dichloro-5-ethenylsulfonyloxyphenyl)-3-methyl-4-difluoromethyl-$\Delta^2$-1,2,4-triazolin-5-one (Example 20) in 5 mL of 2-propene-1-ol in the presence of a catalytic amount of powdered potassium hydroxide gave 0.13 g of product as an oil.

The nmr spectrum was consistent with the proposed structure.

EXAMPLE 46

1-(2-Chloro-4-Methyl-4-Methylsulfonyloxyphenyl)-3-Methyl-4-Difluoromethyl-$\Delta^2$-1,2,4-Triazolin-5-One Step 1: 4-Methyl-3-methoxyphenol hydrazine.

The compound was prepared by a method analogous to that of Example 40, Step 1. The reaction of 100 g (0.73 mole) of 4-methyl-3-methoxyaniline and 50.5 g (0.73 mole) of sodium nitrite in the presence of 330 g (1.46 moles) of stannous chloride dihydrate, 1160 mL of concentrated hydrochloric acid and 250 mL of water gave 58.0 g of product as an oil.

The nmr spectrum was consistent with the proposed structure.

Step 2: Pyruvic acid, 4-methyl-3-methoxyphenyl hydrazone.

This compound was prepared by a method analogous to that of Example 40, Step 2. The reaction of 57.6 g (0.378 mole) of 4-methyl-3-methoxyphenyl hydrazine and 33.3 g (0.378 mole) of pyruvic acid in the presence of 400 mL of 1N hydrochloric acid and 400 mL of ethanol gave 59.0 g of product as a solid.

The nmr spectrum was consistent with the proposed structure.

Step 3: 1-(4-Methyl-3-methoxyphenyl)-3-methyl-$\Delta^2$-1,2,4-triazolin-5-one.

This compound was prepared by a method analogous to that of Example 40, Step 3. The reaction of 56.8 g (0.256 mole) of pyruvic acid, 4-methyl-3-methoxyphenyl hydrazone and 70.3 g (0.256 mole) of diphenyl phosphoryl azide in the presence of 25.9 g (0.256 mole) of triethylamine in 1500 mL of toluene gave 75.0 g of damp product; mp 165°–168° C.

The nmr spectrum was consistent with the proposed structure.

Step 4: 1-(4-Methyl-3-methoxyphenyl)-3-methyl-4-difluoromethyl-$\Delta^2$-1,2,4-triazolin-5-one.

This compound was prepared by a method analogous to that of Example 40, Step 4. The reaction of 60.0 g (0.276 mole) of 1-(4-methyl-3-methoxyphenyl)-3-methyl-$\Delta^2$-1,2,4-triazolin-5-one and 60.0 g (0.67 mole) of chlorodifluoromethane in the presence of 60.0 g (1.5 moles) of sodium hydroxide and 60.0 g (0.186 mole) tetrabutylammonium bromide in 2000 mL of cyclohexane gave 18.5 g of product as a solid.

The nmr spectrum was consistent with the proposed structure.

Step 5: 1-(2-Chloro-4-methyl-5-methoxyphenyl)-3-methyl-4-difluoromethyl-$\Delta^2$-1,2,4-triazolin-5-one.

A solution of 15.0 g (0.056 mole) of 1-(4-methyl-3-methoxyphenyl)-3-methyl-4-difluoromethyl-$\Delta^2$-1,2,4-triazolin-5-one and 7.5 g (0.056 mole) of sulfuryl chloride in 100 mL of chloroform was stirred at ambient temperature for 2 hours. The reaction mixture was concentrated under reduced pressure to give a residue. The residue was dissolved in methylene chloride and washed with aqueous 10% sodium hydroxide. The organic layer was dried with magnesium sulfate and filtered. The filtrate was concentrated under reduced pressure to give 16.5 g of product as a solid.

The nmr spectrum was consistent with the proposed structure.

Step 6: 1-(2-Chloro-4-methyl-5-hydroxyphenyl)-3-methyl-4-difluoromethyl-$\Delta^2$-1,2,4-triazolin-5-one.

This compound was prepared by a method analogous to that of Example 40, Step 6. The reaction of 16.0 g (0.053 mole) of 1-(2-chloro-4-methyl-5-methoxyphenyl)-3-methyl-4-difluoromethyl-$\Delta^2$-1,2,4-triazolin-5-one and 39.6 g (0.158 mole) of boron tribromide in 100 mL of methylene chloride gave 10.5 g of product as a solid.

The nmr spectrum was consistent with the proposed structure.

Step 7: 1-(2-Chloro-4-methyl-5-methylsulfonyloxyphenyl)-3-methyl-4-difluoromethyl-$\Delta^2$-1,2,4-triazolin-5-one.

This compound was prepared by a method analogous to that of Example 2. The reaction of 0.8 g (0.003 mole) of 1-(2-chloro-4-methyl-5-hydroxyphenyl)-3-methyl-4-difluoromethyl-$\Delta^2$-1,2,4-triazolin-5-one and 0.32 g (0.003 mole) of methanesulfonyl chloride in the presence of 0.07 g (0.003 mole) of sodium hydride in dimethylformamide gave 0.4 g of product as an oil.

The nmr spectrum was consistent with the proposed structure.

EXAMPLE 47

1-(2-Chloro-4-Methyl-5-Dimethylaminosulfonyloxyphenyl)-3-Methyl-4-Difluoromethyl-$\Delta^2$-1,2,4-Triazolin-5-One This compound was prepared by the reaction of 0.75 g (0.003 mole) of 1-(2-chloro-4-methyl-5-hydroxyphenyl)-3-methyl-4-difluoromethyl-$\Delta^2$-1,2,4-triazolin-5-one with 0.38 g (0.003 mole) of dimethylaminosulfonyl chloride in the presence of 0.144 g (0.003 mole of NaH) of a 50% dispersion of sodium hydride in oil in 8 mL of dimethylformamide; yield 0.58 g, mp 93°–95° C.

The nmr spectrum was consistent with the proposed structure.

EXAMPLE 48

1-(2-Chloro-4-Methyl-5-Ethylsulfonyloxyphenyl)-3-Methyl-4-Difluoromethyl-$\Delta^2$-1,2,4-Triazolin-5-One This compound was prepared by the reaction of 0.8 g (0.003 mole) of 1-(2-chloro-4-methyl-5-hydroxyphenyl)-3-methyl-4-difluoromethyl-$\Delta^2$-1,2,4-triazolin-5-one with 0.36 g (0.003 mole) of ethanesulfonyl chloride in the presence of 0.29 g (0.003 mole) of triethylamine in 20 mL of tetrahydrofuran; yield 0.94 g as an oil.

The nmr spectrum was consistent with the proposed structure.

EXAMPLE 49

1-(2-Chloro-4-Methyl-5-Chloromethylsulfonyloxyphenyl)-3-Methyl-4-Difluoromethyl-$\Delta^2$-1,2,4-Triazolin-5-One This compound was prepared by the reaction of 0.8 g (0.003 mole) of 1-(2-chloro-4-methyl-5-hydroxyphenyl)-3-methyl-4-difluoromethyl-$\Delta^2$-1,2,4-triazolin-5-one with 0.42 g (0.003 mole) of chloromethylsulfonyl chloride in the presence of 0.29 g (0.003 mole) of triethylamine in 20 mL of tetrahydrofuran; yield 0.46 g as an oil.

The nmr spectrum was consistent with the proposed structure.

EXAMPLE 50

1-{2,4-Dichloro-5-[2-(2-Propynyloxy)Ethylsulfonyloxy]Phenyl}-3-Methyl-4-Difluoromethyl-$\Delta^2$-1,2,4-Triazolin-5-One By the method of Example 44, the reaction of 0.5 g (0.0013 mole) of 1-(2,4-dichloro-5-ethylsulfonyloxyphenyl)-3-methyl-4-difluoromethyl-$\Delta^2$-1,2,4-triazolin-5-one with 3.2 g of propargyl alcohol in the presence of a catalytic amount of powdered potassium hydroxide gave 0.46 g of product as an oil.

The nmr spectrum was consistent with the proposed structure.

EXAMPLE 51

1-{2,4-Dichloro-5-[2-(Methoxycarbonylmethoxy)Ethylsulfonyloxy]Phenyl}-3-Methyl-4-Difluoromethyl-$\Delta^2$-1,2,4-Triazolin-5-One By the method of Example 44, the reaction of 0.25 g (0.0006 mole) of 1-(2,4-dichloro-5-ethenylsulfonyloxyphenyl)-3-methyl-4-difluoromethyl-$\Delta^2$-1,2,4-triazolin-5-one with 2 mL of methyl glycolate in the presence of a catalytic amount of powdered potassium hydroxide gave 0.08 g of product as an oil.

The nmr spectrum was consistent with the proposed structure.

EXAMPLE 52

1-(4-Chloro-2-Fluoro-5-Methylsulfonyloxyphenyl)-3-Methyl-4-Difluoromethyl-$\Delta^2$-1,2,4-Triazolin-5-One Step 1: 4-Chloro-2-fluoro-5-methoxyaniline The intermediate 4-chloro-2-fluoro-5-methoxyaniline was prepared in a five step synthesis from commercially available 2-chloro-4-fluorophenol as detailed by E. Nagano, et al. in European Patent Application No. 69,855, incorporated herein by reference.

Step 2: 4-Chloro-2-fluoro-5-methoxyphenylhydrazine

A stirred solution of 48.0 g (0.27 mole) of 4-chloro-2-fluoro-5-methoxyaniline in 500 mL of concentrated hydrochloric acid was cooled to −5° C. and 23.5 g (0.34 mole) of sodium nitrite in 100 mL of water was added dropwise. After complete addition, the reaction mixture was stirred at 0° C. for one hour. A second solution of 154.0 g (0.68 mole) of stannous chloride in 225 mL of concentrated hydrochloric acid was cooled to 0° C., and the cold diazonium solution prepared above was added to it slowly. After complete addition, the reaction mixture was allowed to warm to ambient temperature. The reaction mixture was filtered to collect a solid. This solid was dissolved in an aqueous 50% sodium hydroxide solution, and the solution extracted with toluene. The toluene extract was dried with magnesium sulfate and filtered. The filtrate was concentrated under reduced pressure to yield 22.4 g of 4-chloro-2-fluoro-5-methoxyphenylhydrazine as a solid.

The nmr spectrum was consistent with the proposed structure.

Step 3: Pyruvic acid, 4-chloro-2-fluoro-5-methoxyphenylhydrazone.

A stirred solution of 21.0 g (0.11 mole) of 4-chloro-2-fluoro-5-methoxyphenylhydrazine and 100 mL of aqueous 10% hydrochloric acid in 100 mL of ethanol was warmed to 40° C., and a solution of 10.0 g (0.114 mole) of pyruvic acid in 20 mL of water was added. Upon complete addition, the reaction mixture was stirred for one hour. An additional 50 mL of water was added and the reaction mixture filtered to collect a solid. The solid was air dried to yield 29.0 g of pyruvic acid, 4-chloro-2-fluoro-5-methoxyphenylhydrazone; mp 166°–169° C.

The nmr spectrum was consistent with the proposed structure.

Step 4: 1-(4-Chloro-2-fluoro-5-methoxyphenyl)-3-methyl-$\Delta^2$-1,2,4-triazolin-5-one.

A stirred solution of 27.0 g (0.104 mole) of pyruvic acid, 4-chloro-2-fluoro-5-methoxphenylhydrazone, 29.0 g (0.105 mole) of diphenylphosphoryl azide, and 11.0 g (0.108 mole) of triethylamine in 500 mL of toluene was heated under reflux for four hours. The reaction mixture was cooled to ambient temperature and extracted with an aqueous 10% sodium hydroxide solution. The extract was neutralized with gaseous carbon dioxide, and a solid was collected by filtration. The solid was air dried to yield 11.0 g of 1-(4-chloro-2-fluoro-5-methoxyphenyl)-3-methyl-$\Delta^2$-1,2,4-triazolin-5-one, mp 193°–195° C.

The nmr spectrum was consistent with the proposed structure.

Step 5: 1-(4-Chloro-2-fluoro-5-methoxyphenyl-3-methyl-4-difluoromethyl-$\Delta^2$-1,2,4-triazolin-5-one.

A stirred mixture of 10.0 g (0.039 mole) of 1-(4-chloro-2-fluoro-5-methoxyphenyl)-3-methyl-$\Delta^2$-1,2,4-triazolin-5-one, 10.0 g (0.31 mole) of tetrabutylammonium bromide and 10.0 g (0.25 mole) of sodium hydroxide in 250 mL of cyclohexane was warmed to 60° C. Chlorodifluoromethane, 10.0 g (0.12 mole) was bubbled into the reaction mixture. After complete addition, the reaction mixture was warmed to reflux and stirred for one hour. The hot solution was decanted from a pot residue and cooled to ambient temperature. Methylene chloride was added to the cooled mixture to dissolve a solid precipitate. The mixture was washed with 10% hydrochloric acid, then with an aqueous 10% sodium hydroxide solution. The organic layer was dried with anhydrous magnesium sulfate and filtered. The filtrate was concentrated under reduced pressure to yield 5.0 g of 1-(4-chloro-2-fluoro-5-methoxyphenyl)-3-methyl-4-difluoromethyl-$\Delta^2$-1,2,4-triazolin-5-one; mp 86°–88° C.

The nmr spectrum was consistent with the proposed structure.

Step 6: 1-(4-Chloro-2-fluoro-5-hydroxyphenyl)-3-methyl-4-difluoromethyl-$\Delta^2$-1,2,4-triazolin-5-one.

A stirred solution of 4.6 g (0.015 mole) of 1-(4-chloro-2-fluoro-5-methoxyphenyl)-3-methyl-4-difluoromethyl-$\Delta^2$-1,2,4-triazolin-5-one in 200 mL of methylene chloride was cooled to 10° C., and a solution of 11.2 g (0.045 mole) of boron tribromide in 45 mL of methylene chloride was added. Upon complete addition, the reaction mixture was stirred for four hours as it warmed to ambient temperature. After this time 100 mL of water was added, and the reaction mixture continued to stir for an additional 18 hours. The organic layer was separated, dried with anhydrous magnesium sulfate, and filtered. The filtrate was concentrated under reduced pressure to yield 4.4 g of 1-(4-chloro-2-fluoro-5-hydroxyphenyl)-4-difluoromethyl-3-methyl-$\Delta^2$-1,2,4-triazolin-5-one; mp 147°–152° C.

The nmr spectrum was consistent with the proposed structure.

Step 7: 1-(4-Chloro-2-fluoro-5-methylsulfonyloxyphenyl-3-methyl-4-difluoromethyl-$\Delta^2$-1,2,4-triazolin-5-one.

This compound was prepared by the reaction of 0.5 g (0.0017 mole) of 1-(4-chloro-2-fluoro-5-hydroxyphenyl)-3-methyl-4-difluoromethyl-$\Delta^2$-1,2,4-triazolin-5-one with 0.2 g (0.00175 mole) of methanesulfonyl chloride in the presence of 0.2 g (0.00175 mole) of triethylamine in 40 mL of tetrahydrofuran; yield 0.62 g as a gum.

The nmr spectrum was consistent with the proposed structure.

EXAMPLE 53

1-(2,4-Dichloro-5-Difluoromethylsulfonyloxyphenyl)-3-Methyl-4-Difluoromethyl-$\Delta^2$-1,2,4-Triazolin-5-One This compound was prepared by the reaction of 0.75 g (0.002 mole) of 1-(2,4-dichloro-5-hydroxyphenyl)-3-methyl-4-difluoromethyl-$\Delta^2$-1,2,4-triazolin-5-one with 0.38 g (0.002 mole) of difluoromethanesulfonyl chloride in the presence of 0.27 g (0.002 mole) of triethylamine in 25 mL of tetrahydrofuran; yield 0.53 g mp 95°–97° C.

The nmr spectrum was consistent with the proposed structure.

EXAMPLE 54

1-(2,4-Dichloro-5-Methylsulfonyloxyphenyl)-3-Ethyl-4-Difluoromethyl-$\Delta^2$-1,2,4-Triazolin-5-One Step 1: 1-(2,4-Dichloro-5-hydroxyphenyl)-3-ethyl-4-difluoromethyl-$\Delta^2$-1,2,4-triazolin-5-one.

This compound was prepared by a method similar to that of steps 1–6 of Example 52 starting with 2,4-dichlorophenol and proceeding via the intermediates 2,4-dichloro-5-(1-methylethoxy)aniline (step 1), 2,4-dichloro-5-(1-methylethoxy)phenylhydrazine (step 2), 2-ketobutyric acid 2,4-dichloro-5-(1-methylethoxy)phenylhydrazone (step 3), use 2-ketobutyric acid rather than pyruvic acid), 1-[2,4-dichloro-5-(1-methylethoxy)phenyl]-3-ethyl-$\Delta^2$-1,2,4-triazolin-5-one (step 4), and 1-[2,4-dichloro-5-(1-methylethoxy)phenyl]-3-ethyl-4-difluoromethyl-$\Delta^2$-1,2,4-triazolin-5-one.

Step 2: 1-(2,4-Dichloro-5-methylsulfonyloxyphenyl)-3-ethyl-4-difluoromethyl-$\Delta^2$-1,2,4-triazolin-5-one.

This compound was prepared by the reaction of 0.5 g (0.0015 mole) of the product of step 1 with 0.17 g (0.005 mole) of methanesulfonyl chloride in the presence of 0.16 g (0.0016 mole) of triethylamine in 20 mL of tetrahydrofuran; yield 0.27 g, mp 118°–123° C.

The nmr spectrum was consistent with the proposed structure.

HERBICIDAL ACTIVITY

The test species used in demonstrating the herbicidal activity of compounds of this invention include cotton (*Gossypium hirsutum* var. Stoneville), soybean (*Glycine max* var. Williams), field corn (*Zea mays* var. Agway 595S), rice (*Oryza sativa* var. Labelle), wheat (*Triticum aestivium* var. Prodax), field bindweed (*Convolvulus arvensis*), morningglory (*Ipomea lacunosa* or *Ipomea hederacea*), velvetleaf (*Abutilon theophrasti*), barnyardgrass (*Echinocloa crus galli*), green foxtail (*Setaria viridis*), johnsongrass (*Sorghum halepense*), and yellow nutsedge (*Cyperus esculentus*).

Procedure

Two disposable fiber flats (8 cm×15 cm×25 cm) for each rate of application for each candidate herbicide for preemergence testing were filled to an approximate depth of 6.5 cm with steam sterilized sandy loam soil. The soil was leveled and impressed with a template to provide six evenly spaced furrows 13 cm long and 0.5 cm deep in each flat. Seeds or tubers of cotton, soybean, corn, rice, wheat, and yellow nutsedge were planted in the furrows of the first flat, and seeds of bindweed, morningglory, velvetleaf, barnyardgrass, green foxtail, and johnsongrass were planted in the furrows of the second flat. The six-row template was again employed to firmly press the seeds or tubers into place. A topping soil of equal portions of sand and sandy loam soil was placed uniformly on top of each flat to a depth of approximately 0.5 cm. Flats for postemergence testing were prepared in the same manner.

The flats for the preemergence test were first watered, then drenched with a solution of test compound as described below. The flats were placed in a greenhouse and watered regularly at the soil surface for 21 days at which time phytotoxicity data were recorded.

The flats for the postemergence test were placed in a greenhouse and watered for 8–10 days, then the foliage of the emerged test plants was sprayed with a solution of the test compound. After spraying,, the foliage was kept for 24 hours, then watered regularly for 21 days, and phytotoxicity data recorded.

In both preemergence and postemergence tests, the candidate herbicides were applied as a aqueous-acetone solutions at rates equivalent to 8.0 kilograms/hectare (kg/ha) and submultiples thereof, i.e., 4.0 kg/ha, 2.0 kg/ha, and so on. Preemergence applications were made as soil drenches using 100 mL of test solution of appropriate concentration for each of the two flats/compound. Postemergence applications were made as foliage sprays using 5 mL of test solution for each of the two flats.

For flats of the size described above, an application rate of 8.0 kg/ha of test compound is equivalent to 0.025 g/flat. A stock solution of 0.2 g of test compound in 40 mL of acetone containing 0.5% v/v of sorbitan monolaurate emulsifier/solubilizer was prepared. For the 8.0 kg/ha preemergence test, 10 mL of the stock solution was diluted with water to give 200 mL of test solution for application as a soil drench to both flats for the compound, 100 mL/flat. For the 8.0 kg/ha postemergence test, 10 mL of the stock solution was used undiluted as a spray, 5 mL/flat. The remaining 20 mL of stock solution was diluted with an equal volume of acetone-emulsifier to give 40 mL of a second stock solution, containing 0.1 g of test compound, and the process above repeated, i.e., 20 mL of the solution being used for the 4.0 kg/ha application rate, and 20 mL for the preparation of lower rate test solutions by the same process.

Herbicidal data at selected application rates are given for various compounds of the invention in the tables below. The test compounds are identified in the tables below by numbers which correspond to those in Table 1 above. Except for Compound 53, Phytotoxicity data were taken as percent kill. For Compound 53, data were recorded as percent control (Table 10). Percent control was determined by a method similar to the 0 to 100 rating system disclosed in "Research Methods In Weed Science," 2nd ed., B. Truelove, Ed.; Southern Weed Science Society; Auburn University, Auburn, Ala., 1977. The present % Control rating system is as follows:

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no recovery | Moderate weed control |
| 70 | | Heavy injury and stand loss | Control somewhat less than satisfactory |
| 80 | Severe effect | Crop nearly destroyed a few survivors | Satisfactory to good weed control |
| 90 | | Only occasional live plants left | Very good to excellent control |
| 100 | Complete effect | Complete crop destruction | Complete weed destruction |

TABLE 2

Preemergence Herbicidal Activity [8.0 kg/ha]

Compound No. % Kill at 8.0 kg/ha

| Species | 4 | 5 | 8 | 10 | 12 | 13 | 14 | 16 | 21 | 25 | 26 | 27 | 28 | 31 | 32 | 33 | 30 |
|---|---|---|---|---|---|---|---|---|---|---|---|---|---|---|---|---|---|
| Cotton | 0 | 0 | 100 | 0 | 30 | 0 | 0 | 0 | 0 | 0 | 0 | 0 | 0 | 0 | 0 | 20 | 0 |
| Soybean | 10 | 0 | 100 | 70 | 100 | 80 | 60 | 20 | 0 | 10 | 0 | 0 | 0 | 0 | 0 | 80 | 80 |
| Field Corn | 30 | 60 | 100 | 100 | 30 | 0 | 0 | 100 | 100 | 0 | 0 | 0 | 0 | 0 | 0 | 100 | 80 |
| Rice | 0 | 10 | 10 | 20 | 50 | 10 | 0 | 20 | 60 | 0 | 0 | 0 | 0 | 0 | 0 | 30 | 10 |
| Wheat | 0 | 20 | 100 | 100 | 100 | 100 | 20 | 30 | 80 | 0 | 0 | 0 | 0 | 0 | 0 | 90 | 40 |
| Field Bindweed | 20 | 100 | 60 | 90 | 100 | 100 | 20 | 20 | 0 | 0 | 0 | 0 | 0 | 0 | 0 | 0 | 0 |
| Morningglory | 100 | 100 | 100 | 70 | 100 | 100 | 40 | 20 | 0 | 0 | 0 | 0 | 0 | 10 | 0 | 80 | 10 |
| Velvetleaf | 100 | 100 | 100 | 100 | 100 | 100 | 100 | 100 | 100 | 0 | 65 | 0 | 90 | 100 | 40 | 100 | 100 |
| Barnyardgrass | 50 | 100 | 100 | 100 | 100 | 100 | 100 | 40 | 0 | 15 | 0 | 0 | 60 | 0 | 0 | 100 | 100 |
| Green Foxtail | 100 | 100 | 100 | 100 | 100 | 100 | 100 | 100 | 20 | 100 | 90 | 80 | 100 | 100 | 0 | 100 | 100 |
| Johnsongrass | 100 | 100 | 100 | 10 | 100 | 100 | 80 | 10 | 30 | 60 | 0 | 0 | 75 | 50 | 0 | 100 | 100 |
| Yellow Nutsedge | 0 | 0 | 0 | 0 | 0 | 0 | 0 | 0 | 0 | 0 | 0 | 0 | 0 | 0 | 0 | 70 | 10 |

TABLE 3

Preemergence Herbicidal Activity [4.0 kg/ha]

Compound No. % Kill at 4.0 kg/ha

| Species | 6 | 20 | 23 | 29 | 30 | 35 | 36 | 37 | 38 | 39 | 43 | 44 | 45 | 46 | 47 | 48 | 49 |
|---|---|---|---|---|---|---|---|---|---|---|---|---|---|---|---|---|---|
| Cotton | 0 | 0 | 20 | 0 | 0 | 0 | 0 | 0 | 0 | 0 | 0 | 20 | 10 | 0 | 0 | 0 | 0 |
| Soybean | 0 | 0 | 20 | 0 | 0 | 0 | 0 | 0 | 0 | 50 | 0 | 0 | 100 | 20 | 40 | 60 | 0 |
| Field Corn | 30 | 0 | 50 | 0 | 0 | 0 | 100 | 100 | 100 | 60 | 0 | 30 | 100 | 100 | 100 | 100 | 100 |
| Rice | 0 | 10 | 20 | 0 | 0 | 0 | 90 | 0 | 100 | 90 | 0 | 0 | 100 | 60 | 20 | 95 | 0 |
| Wheat | 20 | 20 | 20 | 0 | 0 | 0 | 100 | 80 | 100 | 100 | 0 | 0 | 100 | 100 | 70 | 100 | 80 |
| Field Bindweed | 30 | 40 | 0 | 80 | 0 | 0 | 50 | 0 | 0 | 0 | 0 | 20 | 100 | 60 | 0 | 100 | 20 |
| Morningglory | 40 | 0 | 0 | 20 | 0 | 0 | 0 | 0 | 50 | 0 | 0 | 0 | 100 | 80 | 70 | 90 | 20 |
| Velvetleaf | 100 | 100 | 100 | 100 | 50 | 0 | 100 | 100 | 100 | 100 | 50 | 100 | 100 | 100 | 100 | 100 | 100 |
| Barnyardgrass | 90 | 0 | 50 | 100 | 40 | 0 | 100 | 95 | 95 | 100 | 40 | 30 | 100 | 100 | 100 | 100 | 100 |
| Green Foxtail | 100 | 100 | 100 | 100 | 70 | 90 | 100 | 100 | 100 | 100 | 100 | 100 | 100 | 100 | 100 | 100 | 100 |
| Johnsongrass | 100 | 90 | 70 | 40 | 70 | 0 | 100 | 20 | 30 | 100 | 100 | 100 | 100 | 100 | 100 | 100 | 100 |
| Yellow Nutsedge | 0 | 0 | 0 | 0 | 0 | 0 | 0 | 0 | 0 | 0 | 0 | 0 | 30 | 0 | 0 | 0 | 0 |

TABLE 4

Preemergence Herbicidal Activity [0.250 kg/ha]

Compound No. % Kill at 0.250 kg/ha

| Species | 2 | 17 | 18 | 19 | 22 | 24 | 40 | 41 | 42 |
|---|---|---|---|---|---|---|---|---|---|
| Cotton | 0 | 0 | 0 | 0 | 0 | 30 | 0 | 0 | 0 |
| Soybean | 0 | 0 | 0 | 0 | 0 | 30 | 0 | 0 | 0 |

TABLE 4-continued

Preemergence Herbicidal Activity [0.250 kg/ha]

% Kill at 0.250 kg/ha

| Species | 2 | 17 | 18 | 19 | 22 | 24 | 40 | 41 | 42 |
|---|---|---|---|---|---|---|---|---|---|
| Field Corn | 0 | 20 | 30 | 50 | 0 | 80 | 100 | 100 | 0 |
| Rice | — | 0 | 0 | 0 | 0 | 20 | 20 | 0 | 0 |
| Wheat | — | 0 | 0 | 0 | 0 | 80 | 40 | 0 | 0 |
| Field Bindweed | 0 | 0 | 0 | 0 | 0 | 20 | 0 | 0 | 0 |
| Morningglory | 0 | 0 | 0 | 0 | 10 | 60 | 0 | 0 | 0 |
| Velvetleaf | 100 | 70 | 0 | 80 | 100 | 100 | 70 | 20 | 0 |
| Barnyardgrass | 0 | 30 | 60 | 0 | 100 | 100 | 100 | 95 | 70 |
| Green Foxtail | 10 | 100 | 100 | 50 | 100 | 100 | 50 | 100 | 80 |
| Johnsongrass | 20 | 70 | 60 | 60 | 95 | 100 | 100 | 100 | 100 |
| Yellow Nutsedge | 0 | 0 | 0 | 0 | 0 | 50 | 0 | 0 | 0 |

TABLE 5

Preemergence Herbicidal Activity [0.125 kg/ha]

% Kill at 0.125 kg/ha

| Species | 1 | 3 | 7 | 9 | 11 | 15 |
|---|---|---|---|---|---|---|
| Cotton | 0 | 0 | 0 | 0 | 0 | 0 |
| Soybean | 0 | 0 | 10 | 0 | 0 | 0 |
| Field Corn | 0 | 0 | 95 | 0 | 30 | 0 |
| Rice | 0 | 50 | 60 | 0 | 20 | 0 |
| Wheat | 0 | 0 | 60 | 0 | 0 | 0 |
| Field Bindweed | 0 | 0 | 0 | 0 | 0 | 0 |
| Morningglory | 0 | 0 | 10 | 0 | 0 | 0 |
| Velvetleaf | 100 | 100 | 100 | 60 | 100 | 0 |
| Barnyardgrass | 100 | 70 | 100 | 65 | 85 | 0 |
| Green Foxtail | 95 | 50 | 100 | 95 | 100 | 70 |
| Johnsongrass | 80 | 30 | 90 | 30 | 95 | 85 |
| Yellow Nutsedge | 0 | 0 | 10 | 0 | 0 | 0 |

TABLE 6

Postemergence Herbicidal Activity [8.0 kg/ha]

% Kill at 8.0 kg/ha

| Species | 1 | 2 | 3 | 4 | 5 | 7 | 8 | 9 | 10 | 11 | 12 | 13 |
|---|---|---|---|---|---|---|---|---|---|---|---|---|
| Cotton | 100 | 0 | 100 | 100 | 40 | 100 | 80 | 50 | 10 | 60 | 60 | 100 |
| Soybean | 50 | 70 | 0 | 0 | 0 | 0 | 0 | 20 | 0 | 20 | 0 | 0 |
| Field Corn | 100 | 100 | 30 | 0 | 0 | 100 | 0 | 0 | 0 | 60 | 30 | 0 |
| Rice | 30 | 95 | 10 | 0 | 0 | 95 | 0 | 0 | 0 | 80 | 0 | 0 |
| Wheat | 100 | 100 | 60 | 10 | 0 | 100 | 70 | 10 | 0 | 70 | 20 | 0 |
| Field Bindweed | 100 | 40 | 95 | 20 | 0 | 100 | 20 | 60 | 0 | 100 | 10 | 0 |
| Morningglory | 100 | 80 | 30 | 0 | 40 | 100 | 0 | 70 | 10 | 100 | 90 | 90 |
| Velvetleaf | 100 | 100 | 100 | 100 | 100 | 100 | 100 | 100 | 90 | 100 | 100 | 100 |
| Barnyardgrass | 100 | 100 | 100 | 40 | 95 | 100 | 95 | 100 | 20 | 100 | 100 | 100 |
| Green Foxtail | 100 | 100 | 100 | 70 | 100 | 100 | 100 | 100 | 100 | 100 | 100 | 95 |
| Johnsongrass | 95 | 100 | 50 | 90 | 100 | 100 | 90 | 100 | 10 | 100 | 100 | 90 |
| Yellow Nutsedge | 90 | 0 | 30 | 0 | 0 | 40 | 0 | 0 | 0 | 0 | 0 | 0 |

| Species | 14 | 15 | 16 | 21 | 25 | 26 | 27 | 28 | 31 | 32 | 33 | 34 |
|---|---|---|---|---|---|---|---|---|---|---|---|---|
| Cotton | 0 | 80 | 80 | 0 | 0 | 0 | 0 | 0 | 20 | 0 | 80 | 20 |
| Soybean | 0 | 0 | 0 | 0 | 0 | 0 | 0 | 0 | 0 | 0 | 0 | 0 |
| Field Corn | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 30 | 0 |
| Wheat | 0 | 0 | 0 | 0 | 0 | 0 | 0 | 0 | 0 | 0 | 0 | 0 |
| Field Bindweed | 0 | 40 | 0 | 0 | 0 | 20 | 0 | 0 | 0 | 0 | 0 | 0 |
| Morningglory | 0 | 80 | 0 | 0 | 0 | 0 | 0 | 0 | 40 | 0 | 70 | 0 |
| Velvetleaf | 100 | 100 | 100 | 70 | 35 | 20 | 10 | 100 | 90 | 100 | 90 | 100 |
| Barnyardgrass | 30 | 60 | 0 | 0 | 0 | 0 | 0 | 0 | 0 | 0 | 40 | 30 |
| Green Foxtail | 50 | 90 | 100 | 0 | 0 | 10 | 0 | 0 | 0 | 0 | 70 | 70 |
| Johnsongrass | 80 | 40 | 100 | 0 | 0 | 0 | 0 | 0 | 0 | 0 | 40 | 30 |
| Yellow Nutsedge | 0 | 0 | 0 | 0 | 0 | 0 | 0 | 0 | 0 | 0 | 50 | 0 |

TABLE 7

Postemergence Herbicidal Activity [4.0 kg/ha]

% Kill at 4.0 kg/ha

| Species | 6 | 17 | 18 | 19 | 20 | 22 | 23 | 24 | 29 | 30 | 35 | 36 | 37 |
|---|---|---|---|---|---|---|---|---|---|---|---|---|---|
| Cotton | 20 | 50 | 60 | 90 | 20 | 50 | 30 | 90 | 90 | 0 | 0 | 80 | 60 |
| Soybean | 0 | 0 | 10 | 10 | 0 | 40 | 0 | 65 | 0 | 0 | 0 | 0 | 0 |
| Field Corn | 0 | 0 | 10 | 10 | 0 | 50 | 0 | 100 | 0 | 0 | 0 | 0 | 0 |
| Rice | 0 | 0 | 30 | 30 | 0 | 70 | 40 | 30 | 0 | 0 | 0 | 90 | 0 |
| Wheat | 0 | 0 | 10 | 30 | 0 | 50 | 0 | 100 | 0 | 0 | 0 | 80 | 0 |
| Field Bindweed | 0 | 50 | 80 | 30 | 0 | 70 | 0 | 95 | 0 | 0 | 90 | 50 | 0 |
| Morningglory | 0 | 40 | 95 | 60 | 0 | 80 | 60 | 90 | 20 | 0 | 0 | 20 | 0 |
| Velvetleaf | 100 | 100 | 100 | 100 | — | 100 | 100 | 100 | 100 | — | 10 | 100 | 90 |
| Barnyardgrass | 0 | 0 | 10 | 30 | 0 | 100 | 0 | 100 | 0 | 0 | 0 | 95 | 0 |
| Green Foxtail | 0 | 100 | 100 | 30 | 0 | 100 | 40 | 100 | 60 | — | 0 | 100 | 50 |
| Johnsongrass | 0 | 0 | 30 | 40 | 0 | 90 | 0 | 40 | 0 | 0 | 0 | 80 | 0 |
| Yellow Nutsedge | 0 | 0 | 0 | 0 | 0 | 20 | 0 | 50 | 0 | 0 | 0 | 0 | 0 |

TABLE 7-continued

Postemergence Herbicidal Activity [4.0 kg/ha]

| | Compound No. % Kill at 4.0 kg/ha | | | | | | | | | | | |
|---|---|---|---|---|---|---|---|---|---|---|---|---|
| Species | 38 | 39 | 40 | 41 | 42 | 43 | 44 | 45 | 46 | 47 | 48 | 49 |
| Cotton | 80 | 70 | 20 | 20 | 20 | 60 | 100 | 100 | 100 | 100 | 100 | 70 |
| Soybean | 20 | 0 | 0 | 0 | 0 | 0 | 80 | 40 | 0 | 10 | 20 | 70 |
| Field Corn | 100 | 30 | 0 | 30 | 0 | 0 | 0 | 100 | 100 | 30 | 100 | 60 |
| Rice | 10 | 0 | 0 | 0 | 0 | 0 | 0 | 30 | 30 | 0 | 0 | 0 |
| Wheat | 20 | 40 | 0 | 20 | 0 | 0 | 10 | 100 | 100 | 70 | 50 | 0 |
| Field Bindweed | 20 | 40 | 0 | 30 | 0 | 100 | 100 | 100 | 80 | 20 | 80 | 30 |
| Morningglory | 50 | 40 | 0 | 0 | 0 | 0 | 100 | 100 | 100 | 40 | 80 | 60 |
| Velvetleaf | 100 | 100 | 95 | 100 | 90 | 40 | 100 | 100 | 100 | 100 | 100 | 100 |
| Barnyardgrass | 100 | 100 | 20 | 40 | 0 | 0 | 30 | 100 | 100 | 100 | 100 | 100 |
| Green Foxtail | 30 | 100 | 90 | 100 | 95 | 25 | 95 | 100 | 100 | 100 | 100 | 100 |
| Johnsongrass | 90 | 100 | 0 | 60 | 90 | 0 | 70 | 100 | 100 | 100 | 95 | 100 |
| Yellow Nutsedge | 0 | 0 | 0 | 0 | 0 | 0 | 0 | 80 | 0 | 0 | 0 | 0 |

TABLE 8

Preemergence Herbicidal Activity [2.0 kg/ha]

| | Compound No. % Kill at 2.0 kg/ha | | | |
|---|---|---|---|---|
| Species | 50 | 51 | 52 | 54 |
| Cotton | 0 | 70 | 30 | 0 |
| Soybean | 80 | 100 | 100 | 0 |
| Field Corn | 100 | 100 | 100 | 100 |
| Rice | 100 | 50 | 95 | 80 |
| Wheat | 100 | 100 | 100 | 100 |
| Field Bindweed | 50 | 50 | 100 | 0 |
| Morningglory | 40 | 100 | 100 | 0 |
| Velvetleaf | 100 | 100 | 100 | 100 |
| Barnyardgrass | 95 | 95 | 100 | 100 |
| Green Foxtail | 100 | 95 | 100 | 100 |
| Johnsongrass | 100 | 100 | 100 | 100 |
| Yellow Nutsedge | 30 | 30 | 100 | 0 |

TABLE 9

Postemergence Herbicidal Activity [2.0 kg/ha]

| | Compound No. % Kill at 2.0 kg/ha | | | |
|---|---|---|---|---|
| Species | 50 | 51 | 52 | 54 |
| Cotton | 100 | 100 | 100 | 80 |
| Soybean | 40 | 80 | 100 | 20 |
| Field Corn | 100 | 100 | 100 | 70 |
| Rice | 100 | 100 | 100 | 60 |
| Wheat | 100 | 100 | 100 | 70 |
| Field Bindweed | 100 | 90 | 100 | 30 |
| Morningglory | 60 | 70 | 100 | 0 |
| Velvetleaf | 100 | 100 | 100 | 90 |
| Barnyardgrass | 100 | 100 | 100 | 30 |
| Green Foxtail | 100 | 100 | 100 | 100 |
| Johnsongrass | 100 | 100 | 100 | 70 |
| Yellow Nutsedge | 0 | 0 | 100 | 0 |

TABLE 10

Efficacy Of Compound 53

| | % Control at 1.0 kg/ha | |
|---|---|---|
| Species | Pre | Post |
| Cotton | 20 | 90 |
| Soybean | 30 | 60 |
| Field Corn | 80 | 70 |
| Rice | 60 | 50 |
| Wheat | 30 | 20 |
| Field Bindweed | 30 | 60 |
| Morningglory | 30 | 70 |
| Velvetleaf | 100 | 90 |
| Barnyardgrass | 70 | 100 |
| Green Foxtail | 100 | 90 |
| Johnsongrass | 70 | 40 |
| Yellow Nutsedge | 20 | 0 |

It is clear that the generic class of aryltriazolinones and sulfur analogs thereof described and illustrated herein is characterized by herbicidal activity, and that the degree of this activity varies among specific compounds within this class and to some extent among the species of plant to which these compounds may be applied. Thus, selection of a specific herbicidal compound for control of a specific plant may readily be made.

For herbicidal application, the active compounds as above defined are formulated into herbicidal compositions, by admixture, in herbicidally effective amounts, with the adjuvants and carriers normally employed for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, powdery dusts, as wettable powders, as emulsifiable concentrates, as solutions or as any of several other known types of formulations, depending on the desired mode of application.

For preemergence application these herbicidal compositions are usually applied either as sprays, dusts, or granules in the area in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation, useful herein, is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates, which are homogeneous liquid or paste compositions which are dispersible in water or other dispersant, and may consist entirely of the herbicidal compound and a liquid or solid emulsifying agent, or may also contain a liquid carrier, such as xylene, heavy aromatic naphthas, isophorone, and other non-volatile organic solvents. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises form 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds.

The active herbicidal compounds of this invention may be formulated and/or applied with insecticides, fungicides, nematocides, plant growth regulators, fertilizers, and other agricultural chemicals and may be used as effective soil sterilants as well as herbicidally. In applying an active compound of this invention, whether formulated alone or with other agricultural chemicals, an effective amount and concentration of the aryl-triazolinone is of course employed.

It is apparent that various modifications may be made in the formulation and application of the novel compounds of this invention, without departing from the inventive concepts herein, as defined in the following claims.

I claim:

1. An herbicidal compound of the formula

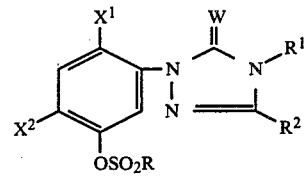

in which $X^1$ and $X^2$ are independently selected from halogen, haloalkyl and alkyl;

W is oxygen;

R is alkyl, haloalkyl, cyanoalkyl;

$R^1$ is alkyl, haloalkyl, cyanoalkyl, alkenyl, alkynyl, or a group of the formula —alkyl—$Y^1$—$R^6$;

$R^2$ is alkyl, cyanoalkyl, haloalkyl, arylalkyl, or a group of the formula —alkyl—$Y^2$—$R^7$;

$R^6$, $R^7$ are independently alkyl, alkoxycarbonylalkyl, alkenyl, or alkynyl; and $Y^1$, $Y^2$ are independently oxygen or $S(O)_r$ in which r is 0 to 2.

2. The compound of claim 1 in which $X^1$ and $X^2$ are independently selected from halogen, haloalkyl of 1 to 3 carbon atoms, and alkyl of 1 to 5 carbon atoms;

R is alkyl of 1 to 8 carbon atoms, haloalkyl, or oganoalkyl wherein each alkyl is of 1 to 5 carbon atoms, $R^1$ is alkyl or haloalkyl of 1 to 5 carbon atoms, cyanoalkyl of 1 to 3 alkyl carbon atoms, alkenyl or alkynyl of 2 to 5 carbon atoms, or a group $(CH_2)_n$—$Y^1$—$R^6$ wherein n is 1 to 5;

$R^2$ is alkyl, haloalkyl, cyanoalkyl, or arylalkyl wherein each alkyl is of 1 to 3 carbon atoms, or a group $(CH_2)_n$—$Y^2$—$R^7$ wherein n is 1 to 5;

$R^6$, $R^7$ are independently alkyl of 1 to 5 carbon atoms, alkenyl or alkynyl of 2 to 5 carbon atoms or a radical —$CH(R^9)CO_2R^{10}$;

$R^9$ is hydrogen or alkyl of 1 to 4 carbon atoms;

$R^{10}$ is alkyl of 1 to 4 carbon atoms; and $Y^1$, $Y^2$ are independently oxygen or $S(O)_r$ in which r is 0 to 2.

3. The compound of claim 2 in which R is alkyl of 1 to 5 carbon atoms, haloalkyl of 1 to 3 carbon atoms, cyanoalkyl of 1 to 3 alkyl carbon atoms.

4. The compound of claim 3 in which R is methyl, ethyl, propyl, 1-methylethyl, butyl, 2-methylpropyl, 1-methylpropyl, 3-methylbutyl, chloromethyl, dichloromethyl, 3-chloropropyl, bromomethyl difluoromethyl trifluoromethyl, or cyanomethyl.

5. The compound of claim 4 in which R is methyl.

6. The compound of claim 2 in which $X^1$ and $X^2$ are the same and are selected from fluorine, chlorine, and bromine, or $X^1$ and $X^2$ are different and $X^1$ is fluorine or chlorine and $X^2$ is chlorine, bromine, haloalkyl, or alkyl.

7. The compound of claim 6 in which for $X^2$ haloalkyl is difluoromethyl and alkyl is methyl.

8. The compound of claim 7 in which $X^1$ is fluorine and $X^2$ is chlorine.

9. The compound of claim 2 in which $R^1$ is alkyl of 1 to 5 carbon atoms, haloalkyl of 1 to 3 carbon atoms and one or more halogen atoms selected independently from fluorine and chlorine, cyanoalkyl of 1 to 3 alkyl carbon atoms, alkenyl or alkynyl of 3 to 5 carbon atoms, or a group —$(CH_2)_2$—$Y^1$—$R^6$ in which $Y^1$ is oxygen or sulfur and $R^6$ is alkyl of 1 to 5 carbon atoms.

10. The compound of claim 9 in which $R^1$ is alkyl of 1 to 3 carbon atoms, fluoroalkyl of 1 to 3 carbon atoms, cyanomethyl, 2-propenyl, 2-propynyl, or a group —$(CH_2)_2$—$Y^1$—$R^6$ in which $R^6$ is methyl or ethyl.

11. The compound of claim 10 in which $R^1$ is difluoromethyl, 3-fluoropropyl, or 2-propenyl.

12. The compound of claim 11 in which $R^1$ is difluoromethyl.

13. The compound of claim 2 in which $R^2$ is alkyl of 1 to 3 carbon atoms,, haloalkyl of 1 to 3 carbon atoms, cyanoalkyl of 1 to 3 alkyl carbon atoms, benzyl, or a group —$(CH_2)_n$—$Y^2$—$R^7$ in which n is 1 or 2, $Y^2$ is oxygen or sulfur, and $R^7$ is alkyl of 1 to 5 carbon atoms.

14. The compound of claim 13 in which $R^2$ is methyl, fluoroalkyl of 1 to 3 carbon atoms, cyanomethyl, or a group —$(CH_2)_n$—$Y^2$—$R^7$ in which $R^7$ is methyl or ethyl.

15. The compound of claim 14 in which $R^2$ is methyl, fluoromethyl, or difluoromethyl.

16. The compound of claim 15 in which $R^2$ is methyl.

17. The compound of claim 2 in which $X^1$ and $X^2$ are the same and are selected from fluorine, chlorine, and bromine, or $X^1$ and $X^2$ are different and $X^1$ is fluorine or chlorine and $X^2$ is chlorine, bromine, haloalkyl, or alkyl;
W is oxygen;
R is alkyl of 1 to 8 carbon atoms of 1 to 5 alkyl carbonators or cyanoalkyl, of 1 to 5 alkyl carbon atoms;
$R^1$ is alkyl of 1 to 5 carbon atoms, haloalkyl of 1 to 3 carbon atoms and one or more halogen atoms selected independently from fluorine and chlorine, cyanoalkyl of 1 to 3 alkyl carbon atoms, alkenyl or alkynyl of 3 to 5 carbon atoms, or a group —$(CH_2)_2$—$Y^1$—$R^6$;
$R^2$ is alkyl of 1 to 3 carbon atoms, haloalkyl of 1 to 3 carbon atoms, cyanoalkyl of 1 to 3 alkyl carbon atoms, benzyl, or a group —$(CH_2)_n$—$Y^2$—$R^7$ in which n is 1 or 2;
$R^6$ and $R^7$ are independently alkyl of 1 to 5 carbon atoms; and $Y^1$ and $Y^2$ are independently oxygen or sulfur.

18. The compound of claim 17 in which W is oxygen; $X^1$ and $X^2$ are the same and are selected from fluorine, chlorine, and bromine, or $X^1$ and $X^2$ are different and $X^1$ is fluorine or chlorine and $X^2$ is chlorine, bromine, difluoromethyl, or methyl;
R is alkyl of 1 to 5 carbon atoms, haloalkyl of 1 to 3 carbon atoms, cyanoalkyl;
$R^1$ is alkyl of 1 to 3 carbon atoms, fluoroalkyl of 1 to 3 carbon atoms, cyanomethyl, 2-propenyl, 2-propynyl, or a group —$(CH_2)_2$—$Y^1$—$R^6$;
$R^2$ is methyl, fluoroalkyl of 1 to 3 carbon atoms, cyanomethyl, or a group —$(CH_2)_n$—$Y^2$—$R^7$; and 19. The compound of claim 19 in which $X^1$ is fluorine and $X^2$ is chlorine;
$R^1$ is difluoromethyl, 3-fluoropropyl, or 2-propenyl; and
$R^2$ is methyl, fluoromethyl, or difluoromethyl.

20. The compound of claim 19 in which R is methyl, ethyl, propyl, 1-methylethyl, butyl, 2-methylpropyl, 1-methylpropyl, 3-methylbutyl, chloromethyl, dichloromethyl, 3-chloropropyl, bromomethyl difluoromethyl trifluoromethyl or, cyanomethyl.

21. The compound of claim 20 in which R is methyl, $R^1$ is difluoromethyl, and $R^2$ is methyl.

22. An herbicidal composition comprising an herbicidally effective amount of a compound of claim 2 in admixture with an inert suitable carrier.

23. A method for controlling undesired plant growth which comprises applying to the locus where control is desired an herbicidally effective amount of the composition of claim 22.

24. The method of claim 23 wherein the locus where control is desired is planted or to be planted with soybeans or corn.

25. The method of claim 24 wherein the locus where control is desired is planted or to be planted with soybeans.

26. The compound of claim 18 in which $X^1$ is fluorine and $X^2$ is bromine;
$R^1$ is difluoromethyl, 3-fluoropropyl, or 2-propenyl; and
$R^2$ is methyl, fluoromethyl, or difluoromethyl.

27. The compound of claim 26 in which R is methyl, $R^1$ is difluoromethyl, and $R^2$ is methyl.

* * * * *